(12) United States Patent
Liu et al.

(10) Patent No.: US 8,765,911 B2
(45) Date of Patent: *Jul. 1, 2014

(54) EVALUATION OF COPOLYMER DIETHYLAMIDE

(71) Applicant: Momenta Pharmaceuticals, Inc., Cambridge, MA (US)

(72) Inventors: Cuihua Liu, Belmont, MA (US); Shiming Dong, North Reading, MA (US); Xiao-Jin Xu, Jamaica Plain, MA (US); Jonathan C. Lansing, Reading, MA (US); Yanjie Jiang, North Chelmsford, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/692,490

(22) Filed: Dec. 3, 2012

(65) Prior Publication Data

US 2014/0046024 A1    Feb. 13, 2014

Related U.S. Application Data

(63) Continuation of application No. 13/584,309, filed as application No. PCT/US2012/046270 on Jul. 11, 2012, now Pat. No. 8,324,348.

(60) Provisional application No. 61/506,494, filed on Jul. 11, 2011, provisional application No. 61/528,477, filed on Aug. 29, 2011.

(51) Int. Cl.
*C07K 1/00* (2006.01)

(52) U.S. Cl.
USPC .......................................................... 530/344

(58) Field of Classification Search
None
See application file for complete search history.

(56) References Cited

U.S. PATENT DOCUMENTS

| | | | |
|---|---|---|---|
| 3,849,550 A | 11/1974 | Teitelbaum et al. |
| 5,112,810 A | 5/1992 | Nagai et al. |
| 5,800,808 A | 9/1998 | Konfino et al. |
| 5,981,589 A | 11/1999 | Konfino et al. |
| 6,048,898 A | 4/2000 | Konfino et al. |
| 6,054,430 A | 4/2000 | Konfino et al. |
| 6,342,476 B1 | 1/2002 | Konfino et al. |
| 6,362,161 B1 | 3/2002 | Konfino et al. |
| 6,514,938 B1 | 2/2003 | Gad et al. |
| 6,620,847 B2 | 9/2003 | Konfino et al. |
| 6,800,287 B2 | 10/2004 | Gad et al. |
| 6,821,745 B2 | 11/2004 | Smith |
| 6,844,314 B2 | 1/2005 | Eisenbach-Schwartz et al. |
| 6,939,539 B2 | 9/2005 | Konfino et al. |
| 7,022,663 B2 | 4/2006 | Gilbert et al. |
| 7,033,582 B2 | 4/2006 | Yong et al. |
| 7,041,472 B2 | 5/2006 | Norioka et al. |
| 7,049,399 B2 | 5/2006 | Bejan et al. |
| 7,053,043 B1 | 5/2006 | Aharoni et al. |
| 7,074,580 B2 | 7/2006 | Gad et al. |
| 7,163,802 B2 | 1/2007 | Gad et al. |
| 7,199,098 B2 | 4/2007 | Konfino et al. |
| 7,329,353 B2 | 2/2008 | Dillon et al. |
| 7,427,600 B2 | 9/2008 | Mickle et al. |
| 7,495,072 B2 | 2/2009 | Dolitzky |
| 7,560,100 B2 | 7/2009 | Pinchasi et al. |
| 7,615,359 B2 | 11/2009 | Gad et al. |
| 7,732,162 B2 | 6/2010 | Hoffman et al. |
| 7,884,187 B2 | 2/2011 | Zhu et al. |
| 7,906,153 B2 | 3/2011 | Theoharides |
| 7,968,511 B2 | 6/2011 | Vollmer |
| 8,008,258 B2 | 8/2011 | Aharoni et al. |
| 8,058,235 B1 | 11/2011 | Coleman et al. |
| 8,324,348 B1 * | 12/2012 | Liu et al. .................. 530/344 |
| 8,470,603 B2 * | 6/2013 | Shriver et al. .................. 436/86 |
| 2002/0115103 A1 | 8/2002 | Gad et al. |
| 2003/0064914 A1 | 4/2003 | Konfino et al. |
| 2003/0153700 A1 | 8/2003 | Wu et al. |
| 2003/0170729 A1 | 9/2003 | Klinger |
| 2004/0091956 A1 | 5/2004 | Bejan et al. |
| 2004/0106554 A1 | 6/2004 | Konfino et al. |
| 2005/0038233 A1 | 2/2005 | Gad et al. |
| 2005/0171286 A1 | 8/2005 | Konfino et al. |
| 2006/0052586 A1 | 3/2006 | Dolitzky |
| 2006/0058225 A1 | 3/2006 | David et al. |
| 2006/0154862 A1 | 7/2006 | Ray et al. |
| 2007/0021324 A1 | 1/2007 | Dolitzky |
| 2007/0054857 A1 | 3/2007 | Pinchasi et al. |

(Continued)

FOREIGN PATENT DOCUMENTS

| | | |
|---|---|---|
| EP | 1 408 066 | 4/2004 |
| WO | WO95/31990 | 11/1995 |

(Continued)

OTHER PUBLICATIONS

International Search Report issued in corresponding PCT application No. PCT/US2012/046270 mailed Feb. 1, 2013.

(Continued)

*Primary Examiner* — Marcela M Cordero Garcia
(74) *Attorney, Agent, or Firm* — Fish & Richardson P.C.

(57) ABSTRACT

Methods of analyzing glatiramer acetate (GA) or a polymeric precursor thereof are provided. The methods can include determining a level of one or more diethylamide-modified amino acids in a sample comprising GA or a polymeric precursor thereof, and selecting at least a portion of the sample based on the assessment of the one or more diethylamide-modified amino acids in the sample.

13 Claims, 1 Drawing Sheet

(56) References Cited

U.S. PATENT DOCUMENTS

| | | |
|---|---|---|
| 2007/0059798 A1 | 3/2007 | Gad et al. |
| 2007/0161566 A1 | 7/2007 | Pinchasi |
| 2007/0178113 A1 | 8/2007 | Backstrom et al. |
| 2008/0118553 A1 | 5/2008 | Frenkel et al. |
| 2008/0199848 A1 | 8/2008 | Bode-Boger et al. |
| 2008/0220441 A1 | 9/2008 | Birnbaum et al. |
| 2008/0319092 A1 | 12/2008 | Singh |
| 2009/0099130 A1 | 4/2009 | Demetriou et al. |
| 2009/0237078 A1 | 9/2009 | Shriver et al. |
| 2009/0263347 A1 | 10/2009 | Jiang et al. |
| 2010/0040537 A1 | 2/2010 | Gu et al. |
| 2010/0111952 A1 | 5/2010 | Beckman et al. |
| 2010/0234566 A1 | 9/2010 | Ray et al. |
| 2010/0256039 A1 | 10/2010 | Coleman et al. |
| 2010/0285513 A1 | 11/2010 | Chan et al. |
| 2010/0324265 A1 | 12/2010 | Kota et al. |
| 2011/0183426 A1 | 7/2011 | Chan et al. |

FOREIGN PATENT DOCUMENTS

| | | |
|---|---|---|
| WO | WO03/048735 | 6/2003 |
| WO | WO2004/043995 | 5/2004 |
| WO | WO2006/029393 | 3/2006 |
| WO | WO2006/029411 | 3/2006 |
| WO | WO2006/050122 | 5/2006 |
| WO | WO2006/069739 | 7/2006 |
| WO | WO2006/069765 | 7/2006 |
| WO | WO2006/083608 | 8/2006 |
| WO | WO2007/030573 | 3/2007 |
| WO | WO 2007/127977 | 11/2007 |
| WO | WO2007/127977 | 11/2007 |
| WO | WO2007/146331 | 12/2007 |
| WO | WO 2008/006026 | 1/2008 |
| WO | WO2008/006026 | 1/2008 |
| WO | WO2010/017292 | 2/2010 |

OTHER PUBLICATIONS

Written Opinion issued in corresponding PCT application No. PCT/US2012/046270 mailed Feb. 1, 2013.

Aventis Pharmaceuticals, Inc., National Drug Code (NDC) 0088-1153-30 (Copaxone®) Label, Version 1 (published Jul. 25, 2006).

Varkony, H., et al, "The glatiramoid class of immunomodulator drugs," Expert Opinion on Pharmacotherapy (Mar. 2009) 10(4):657-668.

Schechter, Bilha; Schechter, Israel; Ramachandran, J., Conway-Jacobs, A., "Synthetic antigens with sequential and conformation-dependent determinants containing the same L-tyrosyl-L-alanyl-L-glutamyl sequence," Eur J Biochem (1971) 20:309-320.

Teitelbaum, D., et al, "Suppression of experimental allergic encephalomyelitis by a synthetic polypeptide," Eur J Immunol (1971) 1(4):242-248.

Sorup, Per, Junager, Finn, and Hvidt, Aase, "Physicochemical studies of a branched polypeptide antigen: poly(1-Tyr,1-Glu)-poly(dl-Ala)—poly(1-Lys)," Biochimica et Biophysica Acta (BBA)—Protein Structure (Sep. 27, 1977) 494(1):9-18.

Hirschmann, Ralph, Schwam, Harvey, Strachan, R.G., "Controlled synthesis of peptides in aqueous medium. VIII. Preparation and use of novel .alpha.-amino acid N-carboxyanhydrides," J Am Chem Soc (1971) 93(11):2746-2754.

Sela, M., Fuchs, S., Amon, R, "Studies on the chemical basis of the antigenicity of proteins, 5. Synthesis, characterization and immunogenicity of some multichain and linear polypeptides containing tyrosine," Biochem J (1962) 85:223-235.

Teitelbaum, D., Arnon, R., Sela, M., "Copaxone," Comprehensive Medicinal Chemistry II (2007) 8:173-185.

Deming, Timothy J., "Synthetic polypeptides for biomedical applications," Progress in Polymer Science (Aug.-Sep. 2007) 32(8-9):858-875.

Johnson, Kenneth, "Glatiramer acetate for treatment of relapsing-remitting multiple sclerosis," Expert Review of Neurotherapeutics (Apr. 2012) 12(4):371-384.

Suzuki et al., Quantitative Analysis of Pyroglutamic Acid in Peptides, J. Agric. Food Chem., 47(8):3248-3251 (1999).

Bogunovic et al., "Comparative Quantitative Mass Spectrometry Analysis of MHC Class II-Associated Peptides Reveals a Role of GILT in Formation of Self-Peptide Repertoire," PLoS ONE 5(5):e10599 (2010) http://www.plosone.org/article/info%3Adoi%2F10.1371%2Fjournal.pone.0010599.

Busby et al., "An Enzyme(s) That Converts Glutaminyl-peptides into Pyroglutamyl-peptides," The Journal of Biological Chemistry, The American Society of Biological Chemists, Inc., 262(18):8532-8536 (1987).

Gawlik et al., "Autocatalytic Activation of the Furin Zymogen Requires Removal of the Emerging Enzyme's N-Terminus from the Active Site," PLoS ONE 4(4):e5031 (2009) http://www.plosone.org/article/info%3Adoi%2F10.1371%2Fjournal.pone.0005031.

Munton et al., "Qualitative and Quantitative Analyses of Protein Phosphorylation in Naïve and Stimulated Mouse Synaptosomal Preparations," American Society for Biochemistry and Molecular Biology, Brain Research Institute, Molecular & Cellular Proteomics, 6.2 (2006) Zurich Switzerland (http://www.mcponline.org/content/6/2/283.full).

Ozols, "Isolation and the complete amino acid sequence of luminal endoplasmic reticulum glucose-6-phosphate dehydrogenase," Procedures of the National Academy of Science, USA, 90:5302-5306 (1993).

Grimmelikhuujzen et al., "Isolation of <Glu-Gly-Arg-Phe-NH2 (AnthoRFamide), a neuropeptide from sea anemones (coelenterate/neurotransmitter/evolution/radioimmunoassay/HPLC)," Procedures of the National Academy of Science, USA, 83:9817-9821 (1986).

Qu et al., "Rapid determination of underivatized pyroglutamic acid, glutamic acid, glutamine and other relevant amino acids in fermentation media by LC-MS-MS," The Royal Society of Chemistry, Analyst (2002) http://www.rsc.org/delivery/_ArticleLinking/DisplayArticleForFree.cfm?doi=b108422b&JournalCode=AN.

Abdelaziz et al., "Inhibition of TNF-alpha production in THP-1 macrophages by glatiramer acetate does not alter their susceptibility to infection by Listeria monocytogenes and does not impair the efficacy of ampicillin or moxifloxacin against intracellular bacteria," J. Anitmicrobial Chem. 54(1):288-289, 2004.

Farina et al., "Treatment of multiple sclerosis with Copaxone (COP): Elispot assay detects COP-induced interleukin-4 and interferon-gamma response in blood cells," Brain 124(4):705-719, 2001.

Hartmann J. et al., "Formation of specific amino acid sequences during carbodiimide-mediated condensation of amino acids in aqueous solution, and computer-simulated sequence generation," Origins of Life, 14, ( 1-4): 213-220, 1984.

Li Q Q et al., "Glatiramer acetate inhibition of tumor necrosis factor-alpha-induced RANTES expression and release from U-251 MG human astrocytic cells," J. of Neurochem. 77(5):1208-1217, 2001.

Milo et al., "Additive effects of copolymer-1 and interferon beta-1b on the immune response to myelin basic protein," J. of Neuroimmunology 61(2):185-193, 1995.

Yang et al., "Drug Acyl Glucuronides: Reactivity and Analytical Implication," Curr. Pharmac. Analysis (Netherlands) 2(3):259-277, 2006.

Express Search, Inc., Accelerated Examination Search Letter, Apr. 20, 2012.

\* cited by examiner

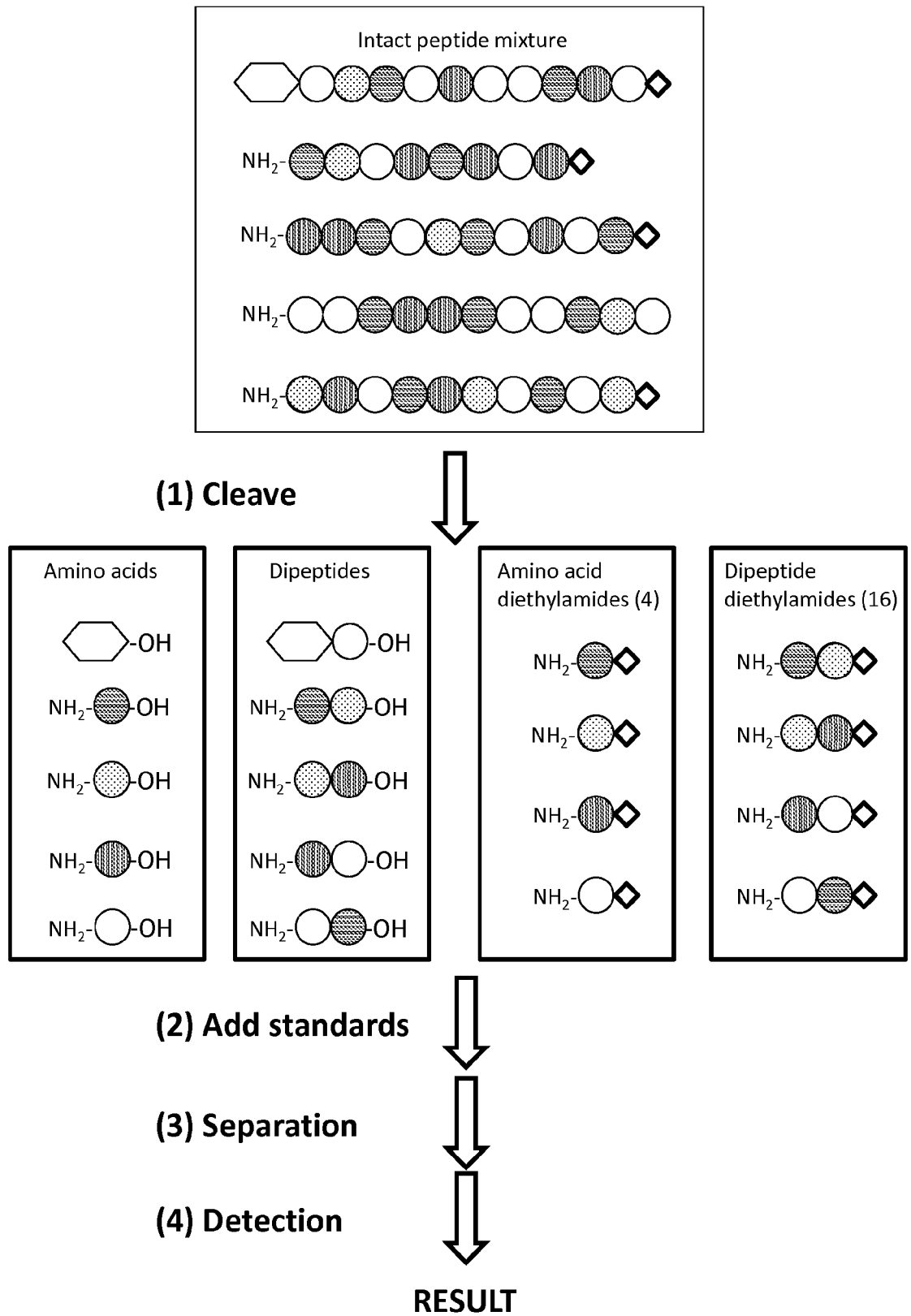

EVALUATION OF COPOLYMER DIETHYLAMIDE

RELATED APPLICATIONS

This application is a continuation of U.S. application Ser. No. 13/584,309, filed Aug. 13, 2012 (now issued U.S. Pat. No. 8,324,348), which is a continuation of International Patent Application No. PCT/US2012/046270, filed Jul. 11, 2012, which claims priority under 35 U.S.C. 119(e) to U.S. Provisional Application Ser. Nos. 61/506,494, filed Jul. 11, 2011, and 61/528,477, filed Aug. 29, 2011. The foregoing applications are herein incorporated by reference in their entireties.

TECHNICAL FIELD

The present disclosure relates to methods for making (e.g., manufacturing or producing) glatiramer acetate (GA), including assessing the distribution of diethylamide (DEA) in GA and/or polymeric precursors of GA.

BACKGROUND

Glatiramer acetate (GA), marketed commercially as COPAXONE®, consists of the acetate salts of synthetic polypeptides containing four naturally occurring amino acids: L-glutamic acid, L-alanine, L-tyrosine, and L-lysine with a reported average molar fraction of 0.141, 0.427, 0.095, and 0.338, respectively. Chemically, GA is designated L-glutamic acid polymer with L-alanine, L-lysine and L-tyrosine, acetate (salt). Its structural formula is:

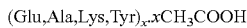

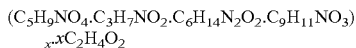

CAS-147245-92-9

Other than molecular weight and amino acid composition, which are specified in the approved label for the product, the label and other available literature for COPAXONE® does not provide detailed information about the physiochemical characteristics of the product.

SUMMARY

The present disclosure provides methods for using the distribution of diethylamide (DEA) in Glatiramer Acetate (GA) and/or polymeric precursors of GA and/or mother liquor resulting from the manufacture of GA in the selection of GA (e.g., upon completion of a manufacturing process) and/or polymeric precursors of GA (e.g., during a manufacturing process); to determine or confirm compliance of GA and/or polymeric precursors of GA with industrial and/or regulatory standards; to assess or confirm manufacturing consistency; as a quality control standard for use during manufacturing and/or against GA. In some embodiments, methods include assessing (e.g., measuring, analyzing, detecting, determining, evaluating, estimating, predicting, monitoring, reviewing, and/or correlating) DEA distribution in Glatiramer Acetate (GA) and/or polymeric precursors of GA and/or mother liquor resulting from the manufacture of GA. Additional applications will be apparent to those of skill in the art based on the disclosure herein.

In some embodiments, the disclosure provides methods for selecting a batch of a composition comprising GA or a polymeric precursor thereof (e.g., referred to as selection methods). These selection methods can include: providing or obtaining a sample of a batch of a composition comprising GA or a polymeric precursor thereof; determining the relative level or ratio of diethylamide-modified alanine:diethylamide-modified lysine:diethylamide-modified glutamic acid:diethylamide-modified tyrosine in the sample; and selecting the batch if (e.g., and only if) the relative level or ratio of diethylamide-modified alanine:diethylamide-modified lysine:diethylamide-modified glutamic acid:diethylamide-modified tyrosine in the sample is about 59.5-76.1%:11.3-17.3%:9.9-15.0%:4.8-7.2%, wherein the total of the relative levels or ratio is 100%. In other embodiments the batch is selected if (e.g., and only if) the relative level or ratio of diethylamide-modified alanine:diethylamide-modified lysine:diethylamide-modified glutamic acid:diethylamide-modified tyrosine in the sample is about 45-95%:9-22%:7-19%:4-9%, wherein the total of the relative levels or ratio is 100%. In other embodiments the batch is selected if (e.g., and only if) the relative level or ratio of diethylamide-modified alanine:diethylamide-modified lysine:diethylamide-modified glutamic acid:diethylamide-modified tyrosine in the sample is about 54-84%:10-19%:9-17%:4-8%, wherein the total of the relative levels or ratio is 100%. In other embodiments the batch is selected if (e.g., and only if) the relative level or ratio of diethylamide-modified alanine:diethylamide-modified lysine:diethylamide-modified glutamic acid:diethylamide-modified tyrosine in the sample is about 60-76%:11-17%:10-15%:5-7%, wherein the total of the relative levels or ratio is 100%.

The present disclosure also provides identification methods that can be used to identify a copolymer as glatiramer acetate. In some cases the copolymer subjected to the identification methods is a copolymer of glutamic acid, alanine, tyrosine, and lysine with a reported average molar fraction of 0.141, 0.427, 0.095, and 0.338, respectively and having a peak average molecular weight of 5,000-7,000. These selection methods can include: providing or obtaining a sample of a batch of a composition comprising a copolymer (e.g., a copolymer of alanine, lysine, glutamic acid and tyrosine); determining the relative level or ratio of diethylamide-modified alanine:diethylamide-modified lysine:diethylamide-modified glutamic acid:diethylamide-modified tyrosine in the sample; and identifying the copolymer as glatiramer acetate if (e.g., and only if) the relative level or ratio of diethylamide-modified alanine:diethylamide-modified lysine:diethylamide-modified glutamic acid:diethylamide-modified tyrosine in the sample is about 59.5-76.1%:11.3-17.3%:9.9-15.0%:4.8-7.2%, wherein the total of the relative levels or ratio is 100%. In other embodiments the copolymer is identified as glatiramer acetate if (e.g., and only if) the relative level or ratio of diethylamide-modified alanine:diethylamide-modified lysine:diethylamide-modified glutamic acid:diethylamide-modified tyrosine in the sample is about 45-95%:9-22%:7-19%:4-9%, wherein the total of the relative levels or ratio is 100%. In other embodiments the copolymer is identified as glatiramer acetate if (e.g., and only if) the relative level or ratio of diethylamide-modified alanine:diethylamide-modified lysine:diethylamide-modified glutamic acid:diethylamide-modified tyrosine in the sample is about 54-84%:10-19%:9-17%:4-8%, wherein the total of the relative levels or ratio is 100%. In other embodiments the copolymer is identified as glatiramer acetate if (e.g., and only if) the relative level or ratio of diethylamide-modified alanine:diethylamide-modified lysine:diethylamide-modified glutamic acid:diethylamide-modified tyrosine in the sample is about 60-76%:11-17%:10-15%:5-7%, wherein the total of the relative levels or ratio is 100%.

In other embodiments, selection methods can include: providing a sample of a batch of a composition comprising GA or a polymeric precursor thereof; determining (e.g., measuring) a level of one or more of diethylamide-modified alanine, diethylamide-modified lysine, diethylamide-modified glutamic acid, and diethylamide-modified tyrosine in the sample; and selecting the batch if (e.g., and only if) the level of the one or more of diethylamide-modified alanine, diethylamide-modified lysine, diethylamide-modified glutamic acid, and diethylamide-modified tyrosine in the sample conforms to a predetermined reference value. In some aspects, the batch is selected if (e.g., and only if): the level of two or more of diethylamide-modified lysine, diethylamide-modified glutamic acid, and diethylamide-modified tyrosine in the sample is about equal to a level shown in Table 1: the level of three or more of diethylamide-modified lysine, diethylamide-modified glutamic acid, and diethylamide-modified tyrosine in the sample is about equal to a level or ratio thereof shown in Table 1; and/or the level of diethylamide-modified lysine, diethylamide-modified glutamic acid, and diethylamide-modified tyrosine in the sample is about equal to a level or shown in Table 1.

In other embodiments, the identification methods can include: providing a sample of a batch of a composition comprising a copolymer (e.g., a copolymer of alanine, lysine, glutamic acid and tyrosine); determining (e.g., measuring) a level of one or more of diethylamide-modified alanine, diethylamide-modified lysine, diethylamide-modified glutamic acid, and diethylamide-modified tyrosine in the sample; and identifying the copolymer as glatiramer acetate if (e.g., and only if) the level of the one or more of diethylamide-modified alanine, diethylamide-modified lysine, diethylamide-modified glutamic acid, and diethylamide-modified tyrosine in the sample conforms to a predetermined reference value. In some aspects, the copolymer is identified as glatiramer acetate (e.g., and only if): the level of two or more of diethylamide-modified lysine, diethylamide-modified glutamic acid, and diethylamide-modified tyrosine in the sample is about equal to a level shown in Table 1: the level of three or more of diethylamide-modified lysine, diethylamide-modified glutamic acid, and diethylamide-modified tyrosine in the sample is about equal to a level or ratio thereof shown in Table 1; and/or the level of diethylamide-modified lysine, diethylamide-modified glutamic acid, and diethylamide-modified tyrosine in the sample is about equal to a level or shown in Table 1.

In further embodiments, selection methods can include: providing a sample of a batch of a composition comprising GA or a polymeric precursor thereof; determining a level of diethylamide-modified alanine in the sample; and selecting the batch if (e.g., and only if): the level of diethylamide-modified alanine in the sample is at least about 45% of the total diethylamide-modified amino acids in the sample; the level of diethylamide-modified alanine in the sample is at least about 50% of the total diethylamide-modified amino acids in the sample; and/or the level of diethylamide-modified alanine in the sample is at least about 65% of the total diethylamide-modified amino acids in the sample. In some aspects, these methods can further include determining a level of one or more of diethylamide-modified lysine, diethylamide-modified glutamic acid, and diethylamide-modified tyrosine in the sample; and selecting the batch if (e.g., and only if): the level of the one or more of diethylamide-modified lysine, diethylamide-modified glutamic acid, and diethylamide-modified tyrosine in the sample is about equal to a level shown in Table 1 or if the ratio of two or more of diethylamide-modified lysine, diethylamide-modified glutamic acid, and diethylamide-modified tyrosine is about equal to a ratio shown in Table 1; the level of two or more of diethylamide-modified lysine, diethylamide-modified glutamic acid, and diethylamide-modified tyrosine in the sample is about equal to a level shown in Table 1; and/or the level of three or more of diethylamide-modified lysine, diethylamide-modified glutamic acid, and diethylamide-modified tyrosine in the sample is about equal to a level or ratio thereof shown in Table 1.

In some embodiments, selection methods can include: providing a sample of a batch of a composition comprising GA or a polymeric precursor thereof; determining the relative level or ratio of two or more of diethylamide-modified alanine, diethylamide-modified lysine, diethylamide-modified glutamic acid, and diethylamide-modified tyrosine in the sample; and selecting the batch if (e.g., and only if): the relative level or ratio of the two or more of diethylamide-modified alanine, diethylamide-modified lysine, diethylamide-modified glutamic acid, and diethylamide-modified tyrosine in the sample conforms to a predetermined reference value; the relative level or ratio of three or more of diethylamide-modified alanine, diethylamide-modified lysine, diethylamide-modified glutamic acid, and diethylamide-modified tyrosine in the sample conforms to a predetermined reference value; the relative level or ratio of diethylamide-modified alanine, diethylamide-modified lysine, diethylamide-modified glutamic acid, and diethylamide-modified tyrosine in the sample conforms to a predetermined reference value. In such embodiments, the or a predetermined reference value can be: a relative level of diethylamide-modified alanine, diethylamide-modified lysine, diethylamide-modified glutamic acid, and/or diethylamide-modified tyrosine shown in Table 1; a relative level or ratio of diethylamide-modified alanine, diethylamide-modified lysine, diethylamide-modified glutamic acid, and diethylamide-modified tyrosine of about 10:2:2:1.

For the selection and identification methods disclosed herein, determination or determining can include cleaving the GA or the polymeric precursor thereof in the sample, e.g., to yield a sample comprising fragments of the GA or fragments of the precursor. Fragments resulting from such cleavage can include diethylamide-modified alanine (Ala-DEA) diethylamide-modified lysine (Lys-DEA), diethylamide-modified glutamic acid (Glu-DEA), and/or diethylamide-modified tyrosine (Tyr-DEA). Such fragments can be or can include 1-mers (e.g., can be a single amino acid with a C-terminal DEA group or can be peptides containing a DEA-modified C-terminal amino acid). For example, fragments can include: a second amino acid selected from alanine, lysine, glutamic acid, and tyrosine; three amino acids, wherein the second and third amino acids are independently selected from alanine, lysine, glutamic acid, and tyrosine; and/or up to 10 amino acids, wherein the amino acids are independently selected from alanine, lysine, glutamic acid, and tyrosine. In any case, a DEA modified peptide will be identified by its C-Terminal-DEA modified amino acid. For example, peptide 'Lys-Lys-Ala-DEA' will be identified as Ala-DEA. In some aspects, selection methods can include a step of isolating or removing diethylamine such that the sample comprising fragments of the GA or fragments of the precursor is substantially free of diethylamine.

Where selection methods include a determining step requiring cleavage of GA or polymeric precursors thereof, such cleavage can be performed enzymatically, chemically, or using physical methods. Exemplary cleavage methods can include contacting the sample with one, two, three, or more proteases (e.g., selected from trypsin, chymotrypsin, elastase, ficin, papain, pepsin, plasmin, thermolysin, endopeptidase, proteinase K, ox bile, lemon pectin, horseradish peroxidase, glu-c, endo lys-C, carboxypeptidase, calpain, and subtilisin) under conditions and for a time sufficient to yield fragments of the GA or fragments of the precursor that include diethylamide-modified alanine, diethylamide-modified lysine, diethylamide-modified glutamic acid, and diethylamide-modified tyrosine. In some aspects, at least one protease is proteinase K.

For the selection methods, determination or determining can further include adding to the sample known concentrations of detectable amino acid or peptide standards that include diethylamide-modified alanine, diethylamide-modified lysine, diethylamide-modified glutamic acid, and diethylamide-modified tyrosine. These detectable amino acid or peptide standards be DEA-modified and can include one, two, three, more than three amino acids, or any number of amino acids required to represent the fragments generated or expected to be generated from the cleavage. In some aspects, detectable amino acids or peptide standards can be isotopically labeled.

Where selection methods include cleavage and addition or use of known concentrations of detectable amino acid or peptide standards, detection can include: detecting peptides corresponding to the detectable amino acid or peptide standards and the detectable amino acid or peptide standards to determine the total amount of diethylamide-modified alanine, diethylamide-modified lysine, diethylamide-modified glutamic acid, and diethylamide-modified tyrosine containing amino acids peptides in the sample; subtracting the known concentrations of the detectable amino acid or peptide standards to determine the levels of diethylamide-modified alanine, diethylamide-modified lysine, diethylamide-modified glutamic acid, and diethylamide-modified tyrosine in the sample; and, optionally, determining the sum of diethylamide-modified alanine amino acids or peptide, the sum of diethylamide-modified lysine amino acids or peptide, the sum of diethylamide-modified glutamic acid amino acids or peptide, and the sum of diethylamide-modified tyrosine containing amino acids and peptides. Detecting peptides, e.g., as part of the detection step, can include: separating diethylamide-modified alanine, diethylamide-modified lysine, diethylamide-modified glutamic acid, and diethylamide-modified tyrosine containing amino acids and peptides and the detectable amino acid or peptide standards using chromatography to yield chromatographically separated samples comprising diethylamide-modified alanine, diethylamide-modified lysine, diethylamide-modified glutamic acid, and diethylamide-modified tyrosine containing amino acids and peptides and the detectable amino acid or peptide standards; and detecting the chromatographically separated samples. Chromatographically separated samples can be assessed, measured, or evaluated using mass spectroscopy analysis. Such mass spectroscopy can include MRM detection or tandem mass spectrophotometry (MS/MS) analysis. Alternatively or in addition, chromatographically separated samples can be assessed, measured, or evaluated using nuclear magnetic resonance (NMR) analysis, infrared spectroscopy, gel electrophoresis, emission spectroscopy, UV-vis spectroscopy, Raman spectroscopy, and antibody detection.

For the selection methods, selection of a batch if (e.g., and only if) the various qualifying parameters are met can include: using at least a portion of the batch in the manufacture or preparation of a GA drug product; formulating at least a portion of the batch for administration to a subject; formulating at least a portion of the batch for injection; and/or releasing at least a portion of the batch for pharmaceutical use. If a batch does not satisfy the various qualifying parameters, then the batch can be withheld and/or discarded.

In some embodiments, selection methods can include: providing a sample of a batch comprising GA or a polymeric precursor thereof; contacting the sample with proteinase K for a time and under conditions sufficient to yield a second sample comprising fragments of the GA or fragments of the precursor, wherein the fragments include diethylamide-modified alanine, diethylamide-modified lysine, diethylamide-modified glutamic acid, and diethylamide-modified tyrosine; adding to the second sample known concentrations of detectable amino acid or peptide standards that represent diethylamide-modified alanine, diethylamide-modified lysine, diethylamide-modified glutamic acid, or diethylamide-modified tyrosine containing amino acids or peptides; chromatographically separating diethylamide-modified alanine, diethylamide-modified lysine, diethylamide-modified glutamic acid, and diethylamide-modified tyrosine containing amino acid or peptides and the detectable amino acid or peptide standards to yield chromatographically separated samples comprising diethylamide-modified alanine, diethylamide-modified lysine, diethylamide-modified glutamic acid, and diethylamide-modified tyrosine containing amino acids and peptides and the detectable amino acid or peptide standards; detecting the chromatographically separated samples; subtracting the known concentrations of the detectable standards to determine the levels of diethylamide-modified alanine, diethylamide-modified lysine, diethylamide-modified glutamic acid, and diethylamide-modified tyrosine; determining the sum of diethylamide-modified alanine amino acids or peptide, the sum of diethylamide-modified lysine amino acids or peptide, the sum of diethylamide-modified glutamic acid amino acids or peptide, and the sum of diethylamide-modified tyrosine amino acids or peptide; and selecting the batch and optionally using at least a portion of the batch in a manufacturing process for GA if the ratio of the sums of two or more, three or more, or all four of diethylamide-modified alanine, diethylamide-modified lysine, diethylamide-modified glutamic acid, and diethylamide-modified tyrosine in the sample are about equal to the ratio between two or more, three or more, or all four of diethylamide-modified alanine, diethylamide-modified lysine, diethylamide-modified glutamic acid, and diethylamide-modified tyrosine shown in Table 1.

In some embodiments, the disclosure provides methods for analyzing a batch of a composition comprising GA or a polymeric precursor thereof (e.g., referred to as analysis methods). These analysis methods can include detection and selection steps or methods disclosed above for the selection methods. In some aspects, selection methods can include: detecting a level of diethylamide-modified alanine in a sample of a batch of a composition comprising GA or a polymeric precursor thereof; and determining if the level of diethylamide-modified alanine in the sample is at least about 45%, 50%, or 55% of the total diethylamide-modified amino acids in the sample. Alternatively or in addition, analysis methods can include: detecting a level of one or more of diethylamide-modified lysine, diethylamide-modified glutamic acid, and diethylamide-modified tyrosine in the sample; and determining if the level of the diethylamide-modified lysine, diethylamide-modified glutamic acid, and diethylamide-modified tyrosine in the sample is about equal to a level shown in Table 1 or if the ratio of two or more of diethylamide-modified lysine, diethylamide-modified glutamic acid, and diethylamide-modified tyrosine is about equal to a ratio shown in Table 1.

In some embodiments, analysis methods can include: detecting a level of one or more of diethylamide-modified alanine, diethylamide-modified lysine, diethylamide-modified glutamic acid, and diethylamide-modified tyrosine in a sample of a batch of a composition comprising GA or a polymeric precursor thereof, and determining if the level of: one or more of diethylamide-modified lysine, diethylamide-modified glutamic acid, and diethylamide-modified tyrosine in the sample is about equal to a level shown in Table 1; two or more of diethylamide-modified lysine, diethylamide-modified glutamic acid, and diethylamide-modified tyrosine in the sample is about equal to a level or ratio shown in Table 1; three or more of diethylamide-modified lysine, diethylamide-modified glutamic acid, and diethylamide-modified tyrosine in the sample is about equal to a level or ratio shown in Table 1; and/or diethylamide-modified lysine, diethylamide-modified glutamic acid, and diethylamide-modified tyrosine in the sample is about equal to a level or ratio shown in Table 1.

In other embodiments, analysis methods can include: detecting the relative level or ratio of diethylamide-modified alanine:diethylamide-modified lysine:diethylamide-modified glutamic acid:diethylamide-modified tyrosine in a sample of a batch of a composition comprising GA or a polymeric precursor thereof; and determining if the relative level or ratio of diethylamide-modified alanine:diethylamide-modified lysine:diethylamide-modified glutamic acid:diethylamide-modified tyrosine in the sample is about 45-95%:9-22%:7-19%:4-9% wherein the total of the relative levels or ratio is 100%.

In further embodiments, analysis methods can include: detecting the relative level or ratio of two or more of diethylamide-modified alanine, diethylamide-modified lysine, diethylamide-modified glutamic acid, and diethylamide-modified tyrosine in a sample of a batch of a composition comprising GA or a polymeric precursor thereof, and determining if the relative level or ratio of: two or more of diethylamide-modified alanine, diethylamide-modified lysine, diethylamide-modified glutamic acid, and diethylamide-modified tyrosine in the sample conforms to a predetermined reference value; three or more of diethylamide-modified alanine, diethylamide-modified lysine, diethylamide-modified glutamic acid, and diethylamide-modified tyrosine in the sample conforms to a predetermined reference value; and/or diethylamide-modified alanine, diethylamide-modified lysine, diethylamide-modified glutamic acid, and diethylamide-modified tyrosine in the sample conforms to a predetermined reference value. In such methods, the predetermined reference value is a relative level of diethylamide-modified alanine, diethylamide-modified lysine, diethylamide-modified glutamic acid, and/or diethylamide-modified tyrosine shown in Table 1. In some instances, the predetermined reference value can be a relative level or ratio of diethylamide-modified alanine, diethylamide-modified lysine, diethylamide-modified glutamic acid, and diethylamide-modified tyrosine of about 10:2:2:1.

In some aspects, analysis methods can include cleaving the GA or the polymeric precursor thereof in the sample to yield or generate a sample comprising fragments of the GA or fragments of the precursor, wherein the fragments include diethylamide-modified alanine, diethylamide-modified lysine, diethylamide-modified glutamic acid, or diethylamide-modified tyrosine. Methods can further include removing diethylamine such that the sample comprising fragments of the GA or fragments of the precursor is substantially free of diethylamine.

For the analysis methods, determination or determining can further include adding to the sample known concentrations of detectable amino acid or peptide standards that include diethylamide-modified alanine, diethylamide-modified lysine, diethylamide-modified glutamic acid, and diethylamide-modified tyrosine. Such detectable standards can be isotopically labeled. In some aspects, detecting peptides corresponding to the detectable amino acid or peptide standards and the detectable amino acid or peptide standards to determine the total amount of diethylamide-modified alanine, diethylamide-modified lysine, diethylamide-modified glutamic acid, and diethylamide-modified tyrosine containing amino acids or peptides in the sample; and subtracting the known concentrations of the detectable amino acid or peptide standards to determine the levels of diethylamide-modified alanine, diethylamide-modified lysine, diethylamide-modified glutamic acid, and diethylamide-modified tyrosine in the sample. Methods can further include determining the sum of diethylamide-modified alanine amino acids or peptide, the sum of diethylamide-modified lysine amino acids or peptide, the sum of diethylamide-modified glutamic acid amino acids or peptide, and the sum of diethylamide-modified tyrosine amino acids or peptide. Where known concentrations of detectable amino acid or peptide standards are used, detection can include: separating diethylamide-modified alanine, diethylamide-modified lysine, diethylamide-modified glutamic acid, and diethylamide-modified tyrosine containing amino acids and peptides and the detectable amino acid or peptide standards using chromatography to yield chromatographically separated samples comprising diethylamide-modified alanine, diethylamide-modified lysine, diethylamide-modified glutamic acid, and diethylamide-modified tyrosine containing peptides and the detectable amino acid or peptide standards; and detecting the chromatographically separated samples.

In some embodiments, the disclosure provides methods of manufacturing GA drug product (e.g., referred to as manufacturing methods). These manufacture methods can include detection and selection steps or methods disclosed above for the selection and/or analysis methods. In some aspects, such methods can include: polymerizing N-carboxy anhydrides of L-alanine, benzyl-protected L-glutamic acid, trifluoroacetic acid (TFA)-protected L-lysine, and L-tyrosine to generate a protected copolymer; treating the protected copolymer to partially depolymerize the protected copolymer and deprotect benzyl protected groups; deprotecting TFA-protected lysines to generate GA; purifying the GA; detecting a level of diethylamide-modified alanine in a sample of the purified GA; and using the GA in the manufacture or preparation of a GA drug product if (e.g., if and only if) the level of diethylamide-modified alanine in the sample is at least about 45%, 55%, or 65% of the total diethylamide-modified amino acids in the sample. In some aspects, there methods can further include: detecting a level of one or more of diethylamide-modified lysine, diethylamide-modified glutamic acid, and diethylamide-modified tyrosine in the sample; and using the GA in the manufacture or preparation of a GA drug product if: the level of the one or more of diethylamide-modified lysine, diethylamide-modified glutamic acid, and diethylamide-modified tyrosine in the sample is about equal to a level shown in Table 1 or if the ratio of two or more of diethylamide-modified lysine, diethylamide-modified glutamic acid, and diethylamide-modified tyrosine is about equal to a ratio shown in Table 1; the level of the two or more of diethylamide-modified lysine, diethylamide-modified glutamic acid, and diethylamide-modified tyrosine in the sample is about equal to a level shown in Table 1; and/or the level of the three or more of diethylamide-modified lysine, diethylamide-modified glutamic acid, and diethylamide-modified tyrosine in the sample is about equal to a level or ratio thereof shown in Table 1.

In some embodiments, manufacturing methods can include: polymerizing N-carboxy anhydrides of L-alanine, benzyl-protected L-glutamic acid, trifluoroacetic acid (TFA)-protected L-lysine, and L-tyrosine to generate a protected copolymer; treating the protected copolymer to partially depolymerize the protected copolymer and deprotect benzyl protected groups; deprotecting TFA-protected lysines to generate GA; purifying the GA; detecting a level of one or more of diethylamide-modified alanine, diethylamide-modified lysine, diethylamide-modified glutamic acid, and diethylamide-modified tyrosine in a sample of the purified GA; and using the GA in the manufacture or preparation of a GA drug product if (e.g., if and only if) the level of one or more of diethylamide-modified lysine, diethylamide-modified glutamic acid, and diethylamide-modified tyrosine in the sample is about equal to a level shown in Table 1, and/or if the ratio of two or more of diethylamide-modified lysine, diethylamide-modified glutamic acid, and diethylamide-modified tyrosine is about equal to a ratio shown in Table 1. In some aspects, these methods can include: using the GA in the manufacture or preparation of a GA drug product if the level of two or more of diethylamide-modified lysine, diethylamide-modified glutamic acid, and diethylamide-modified tyrosine in the sample is about equal to a level shown in Table 1; using the GA in the manufacture or preparation of a GA drug product if the level of three or more of diethylamide-modified lysine, diethylamide-modified glutamic acid, and diethylamide-modified tyrosine in the sample is about equal to a level or ratio thereof shown in Table 1; and/or using the GA in the manufacture or preparation of a GA drug product if the level of diethylamide-modified lysine, diethylamide-modified glutamic acid, and diethylamide-modified tyrosine in the sample is about equal to a level or ratio thereof shown in Table 1.

In other embodiments, manufacturing methods can include: polymerizing N-carboxy anhydrides of L-alanine, benzyl-protected L-glutamic acid, trifluoroacetic acid (TFA)-protected L-lysine, and L-tyrosine to generate a protected copolymer; treating the protected copolymer to partially depolymerize the protected copolymer and deprotect benzyl protected groups; deprotecting TFA-protected lysines to generate GA; purifying the GA; detecting the relative level or ratio of diethylamide-modified alanine:diethylamide-modified lysine:diethylamide-modified glutamic acid:diethylamide-modified tyrosine in a sample of the purified GA; and using the GA in the manufacture or preparation of a GA drug product if the relative level or ratio of diethylamide-modified alanine:diethylamide-modified lysine:diethylamide-modified glutamic acid:diethylamide-modified tyrosine in the sample is about 59.5-76.1%:11.3-17.3%:9.9-15.0%:4.8-7.2%, wherein the total of the relative levels or ratio is 100%. In other embodiments the batch is used if (e.g., and only if) the relative level or ratio of diethylamide-modified alanine:diethylamide-modified lysine:diethylamide-modified glutamic acid:diethylamide-modified tyrosine in the sample is about 45-95%:9-22%:7-19%:4-9%, wherein the total of the relative levels or ratio is 100%. In other embodiments the batch is used if (e.g., and only if) the relative level or ratio of diethylamide-modified alanine:diethylamide-modified lysine:diethylamide-modified glutamic acid:diethylamide-modified tyrosine in the sample is about 54-84%:10-19%:9-17%:4-8%, wherein the total of the relative levels or ratio is 100%. In other embodiments the batch is used if (e.g., and only if) the relative level or ratio of diethylamide-modified alanine:diethylamide-modified lysine:diethylamide-modified glutamic acid:diethylamide-modified tyrosine in the sample is about 60-76%:11-17%:10-15%:5-7%, wherein the total of the relative levels or ratio is 100%.

In further embodiments, manufacturing methods can include: polymerizing N-carboxy anhydrides of L-alanine, benzyl-protected L-glutamic acid, trifluoroacetic acid (TFA)-protected L-lysine, and L-tyrosine to generate a protected copolymer; treating the protected copolymer to partially depolymerize the protected copolymer and deprotect benzyl protected groups; deprotecting TFA-protected lysines to generate GA; purifying the GA; detecting the relative level or ratio of two or more of diethylamide-modified alanine, diethylamide-modified lysine, diethylamide-modified glutamic acid, and diethylamide-modified tyrosine in the sample; and using the GA in the manufacture or preparation of a GA drug product if the relative level or ratio of the two or more of diethylamide-modified alanine, diethylamide-modified lysine, diethylamide-modified glutamic acid, and diethylamide-modified tyrosine in the sample conforms to a predetermined reference value. In some aspects, these methods can include: using the GA in the manufacture or preparation of a GA drug product if the relative level or ratio of three or more of diethylamide-modified alanine, diethylamide-modified lysine, diethylamide-modified glutamic acid, and diethylamide-modified tyrosine in the sample conforms to a predetermined reference value; and/or using the GA in the manufacture or preparation of a GA drug product if the relative level or ratio of diethylamide-modified alanine, diethylamide-modified lysine, diethylamide-modified glutamic acid, and diethylamide-modified tyrosine in the sample conforms to a predetermined reference value. For these methods, the predetermined reference value can be a relative level of diethylamide-modified alanine, diethylamide-modified lysine, diethylamide-modified glutamic acid, and/or diethylamide-modified tyrosine shown in Table 1; and/or a relative level or ratio of diethylamide-modified alanine, diethylamide-modified lysine, diethylamide-modified glutamic acid, and diethylamide-modified tyrosine of about 10:2:2:1.

In some aspects, for the manufacturing methods, detecting DEA-modified amino acids can include cleaving the GA or the polymeric precursor thereof in the sample to yield a sample comprising fragments of the GA or fragments of the precursor, wherein the fragments include diethylamide-modified alanine, diethylamide-modified lysine, diethylamide-modified glutamic acid, and diethylamide-modified tyrosine. Detecting can also optionally include removing diethylamine, such that the sample comprising fragments of the GA or fragments of the precursor is substantially free of diethylamine. In some aspects, wherein GA or the polymeric precursor are cleaved, cleavage can be performed enzymatically, chemically, and/or using physical methods. Where enzymatic cleavage is used, methods can include contacting the sample with one, two, or more proteases (e.g., one or more of trypsin, chymotrypsin, elastase, ficin, papain, pepsin, plasmin, thermolysin, endopeptidase, proteinase K, ox bile, lemon pectin, horseradish peroxidase, glu-c, endo lys-C, carboxypeptidase, calpain, and/or subtilisin) under conditions and for a time sufficient to yield fragments of the GA or fragments of the precursor that include diethylamide-modified alanine, diethylamide-modified lysine, diethylamide-modified glutamic acid, and diethylamide-modified tyrosine. In some instances, the one or more proteases can include proteinase K. Detecting can also include adding to the sample known concentrations of detectable amino acid or peptide standards (e.g., isotopically labeled detectable amino acid or peptide standards) that include diethylamide-modified alanine, diethylamide-modified lysine, diethylamide-modified glutamic acid, and diethylamide-modified tyrosine. Where detectable amino acid or peptide standards are added, detecting peptides can include detecting peptides corresponding to the detectable amino acid or peptide standards and the detectable amino acid or peptide standards to determine the total amount of diethylamide-modified alanine, diethylamide-modified lysine, diethylamide-modified glutamic acid, and diethylamide-modified tyrosine containing amino acids or peptides in the sample; and subtracting the known concentrations of the detectable amino acid or peptide standards to determine the levels of diethylamide-modified alanine, diethylamide-modified lysine, diethylamide-modified glutamic acid, and diethylamide-modified tyrosine in the sample. These methods can further optionally include determining the sum of diethylamide-modified alanine amino acids or peptide, the sum of diethylamide-modified lysine amino acids or peptide, the sum of diethylamide-modified glutamic acid amino acids or peptide, and the sum of diethylamide-modified tyrosine amino acids or peptide. Also, where detectable amino acid or peptide standards are used, detecting peptides corresponding to the detectable amino acid or peptide standards and the detectable amino acid or peptide standards can include: separating diethylamide-modified alanine, diethylamide-modified lysine, diethylamide-modified glutamic acid, and diethylamide-modified tyrosine containing peptides and the detectable standards using chromatography to yield chromatographically separated samples comprising diethylamide-modified alanine, diethylamide-modified lysine, diethylamide-modified glutamic acid, and diethylamide-modified tyrosine containing peptides and the detectable standards; and detecting the chromatographically separated samples. In some aspects, mass spectroscopy analysis can be used. For example, mass spectroscopy can include using MRM detection or tandem mass spectrophotometry (MS/MS). Chromatographically separated samples can also be detected, for example using nuclear magnetic resonance (NMR) analysis, infrared spectroscopy, gel electrophoresis, emission spectroscopy, UV-vis spectroscopy, Raman spectroscopy, and antibody detection.

In some instances, methods include of comparing the determined level to a GA reference standard. In some instances, the reference standard can be or can include a commercially available pharmaceutical preparation of GA (Copaxone®). In another embodiment, the reference standard is a specification for commercial release of a drug product comprising GA. For example, the specification for commercial release can be the specification provided by the U.S. Food & Drug Administration (FDA), e.g., for the pharmaceutical release of GA. In some instances, where the level of the at least one GA-induced polypeptide is within a predetermined range or has a preselected relationship with the reference value, the method can include: providing and/or receiving information regarding the predetermined range or preselected relationship to another party (e.g., a party manufacturing GA), classifying, selecting, accepting, discarding, releasing, or withholding a batch of GA; reprocessing a batch through a previous manufacturing step; processing a batch of GA into drug product, shipping the product from a batch of GA, moving the batch of GA to a new location; or formulating, labeling, packaging, selling, offering for sell, releasing a batch of GA into commerce and/or directing any of the above actions.

In some embodiments, methods include of comparing the determined level to a GA reference standard (e.g., a GA product description in an FDA label, a Physician's Insert, a USP monograph, or an EP monograph) to assess suitability for undergoing a next step, e.g., as disclosed herein. In some embodiments, the methods include recording the determined level in a print or computer-readable medium, e.g., in a test report, Material Safety Data Sheet (MSDS) or Certificate of Testing or Certificate of Analysis (CofA).

In some embodiments, methods of manufacturing a drug product comprising glatiramer acetate include obtaining a sample of a batch of glatiramer acetate; measuring, in the sample of the batch, the level of at least one individual diethylamide-modified amino acid selected from the group consisting of: diethylamide-modified alanine, diethylamide-modified lysine, diethylamide-modified glutamic acid, and diethylamide-modified tyrosine; and processing at least a portion of the batch of glatiramer acetate to produce a drug product comprising glatiramer acetate if at least one of the following measured criteria are met: (i) the level of diethylamide-modified alanine in the sample is 59.5-76.1% of the total diethylamide-modified amino acids in the sample on a mol percent basis; (ii) the level of diethylamide-modified lysine detected in the sample is 11.3-17.3% of the total diethylamide-modified amino acids in the sample on a mol percent basis; (iii) the level of diethylamide-modified glutamic acid detected in the sample is 9.9-15.0% of the total diethylamide-modified amino acids in the sample on a mol percent basis; and (iv) the level of diethylamide-modified tyrosine detected in the sample is 4.8-7.2% of the total diethylamide-modified amino acids in the sample on a mol percent basis, thereby manufacturing a drug product comprising glatiramer acetate. In some instances, at least a portion of the batch of glatiramer acetate is processed to produce a drug product comprising glatiramer acetate if at least two, or at least three, or all four of the criteria are met.

In some instances, the methods of manufacturing a drug product comprising glatiramer acetate include processing at least a portion of the batch of glatiramer acetate to produce a drug product if the level of diethylamide-modified alanine in the sample is 59.5-76.1% of the total diethylamide-modified amino acids in the sample on a mol percent basis.

In other instances, the methods of manufacturing a drug product comprising glatiramer acetate include processing at least a portion of the batch of glatiramer acetate to produce a drug product if the level of diethylamide-modified lysine in the sample is 11.3-17.3% of the total diethylamide-modified amino acids in the sample on a mol percent basis. In certain instances, methods of manufacturing a drug product comprising glatiramer acetate include processing at least a portion of the batch of glatiramer acetate to produce a drug product if the level of diethylamide-modified glutamic acid in the sample is 9.9-15.0% of the total diethylamide-modified amino acids in the sample on a mol percent basis. In other instances, the methods of manufacturing a drug product comprising glatiramer acetate include processing at least a portion of the batch of glatiramer acetate to produce a drug product if the level of diethylamide-modified tyrosine in the sample is 4.8-7.2% of the total diethylamide-modified amino acids in the sample on a mol percent basis.

In other instances, the methods of manufacturing a drug product comprising glatiramer acetate include processing the glatiramer acetate to produce a drug product if the following criteria are met: the level of diethylamide-modified alanine detected in the sample is 59.5-76.1% of the total diethylamide-modified amino acids in the sample on a mol percent basis; the level of diethylamide-modified lysine detected in the sample is 11.3-17.3% of the total diethylamide-modified amino acids in the sample on a mol percent basis; the level of diethylamide-modified glutamic acid detected in the sample is 9.9-15.0% of the total diethylamide-modified amino acids in the sample on a mol percent basis; and the level of diethylamide-modified tyrosine detected in the sample is 4.8-7.2% of the total diethylamide-modified amino acids in the sample on a mol percent basis.

In some embodiments, the step of processing the batch of glatiramer acetate includes combining at least a portion of the glatiramer acetate in the batch with a pharmaceutically acceptable carrier or excipient.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF FIGURES

FIG. 1 is a flow diagram providing an exemplary embodiment of the process disclosed herein. Hexagons represent pyroglutamate. Diamonds represent diethylamide. Circles represent distinct amino acids.

DETAILED DESCRIPTION

Processes for the manufacture of Glatiramer Acetate (GA) generally include:

Polymerization of N-carboxy anhydrides of L-alanine, benzyl-protected L-glutamic acid, trifluoroacetic acid (TFA) protected L-lysine and L-tyrosine (collectively referred to as NCAs) to result in a protected copolymer (Intermediate-1);

Depolymerization and benzyl deprotection of Intermediate-1 using, for example, hydrobromic acid in acetic acid (e.g., phenol treated 33% HBr/acetic acid) to generate Intermediate-2; and Deprotection of the TFA-protected lysines on Intermediate-2 (e.g., by treatment with piperdine) to create Intermediate-3, followed by processing to generate GA and further purification and drying of the isolated GA drug substance.

During polymerization, NCAs are co-polymerized in a predetermined ratio using diethylamine as an initiator. This addition of diethylamine to the reaction mixture results in modification of the C-terminus of a portion of amino acids in the reaction mixture to include diethylamide (DEA). Upon consumption of the NCA components, the reaction mixture is quenched in water. The resulting protected polymer (Intermediate-1) is isolated and dried. During depolymerization and benzyl deprotection, Intermediate-1 is treated with phenol-treated 33% HBr in acetic acid (HBr/AcOH). This results in the cleavage of the benzyl protecting group on the glutamic acids as well as cleavage of peptide bonds throughout the polymer. After a period of time the reaction is quenched with water, and the product polymer is isolated by filtration and washed with water. The product polymer, Intermediate-2, has a reduced molecular weight relative to Intermediate-1. Intermediate-2 is dried before proceeding to deprotection of TFA-protected lysine. During deprotection TFA-protected lysines, Intermediate-2 is treated with aqueous piperidine to remove the trifluoroacetyl group on the lysine. The resulting copolymer, Intermediate-3, is subsequently purified using diafiltration/ultrafiltration and the resulting acetate salt is dried to produce Glatiramer Acetate drug substance. Exemplary methods for the manufacture of GA are known in the art (see, for example, U.S. Pat. No. 3,849,550; WO 95/031990, US 2006/0154862, US 2007/0021324, US 2010/0256039, US 2007/0021324, US 2009/0263347, and US 2010/0256039, and WO 2010/017292 which are hereby incorporated by reference in their entirety).

As disclosed herein, there are certain detectable attributes of GA that are conserved from batch-to-batch. These attributes can be used, e.g., to select GA or polymeric precursors of GA and/or to monitor, assess, and/or evaluate GA process and/or batch quality.

Based on detailed characterization of GA and the GA production process, the present disclosure provides that diethylamide (DEA) distribution on the C-terminus of a portion of amino acids of GA is a conserved detectable attribute, a characteristic, hallmark, and/or a signature (e.g., a structural signature) of GA and/or the GA production process (e.g., polymeric precursors of GA). Accordingly, methods are described herein for assessing or evaluating DEA distribution in GA and/or polymeric precursors of GA, e.g., as a means for selecting GA and/or polymeric precursors of GA.

In some embodiments, methods are described herein for observing DEA distribution in GA and/or polymeric precursors of GA and taking action with respect to the GA and/or polymeric precursors on the basis of the observed DEA distribution therein. For example, methods can include observing data related to DEA distribution in GA and/or polymeric precursors of GA (e.g., electronic data, stored data, and/or printed data) as part of a process for the selection, review (e.g., quality control), and/or manufacture of GA and/or polymeric precursors of GA. Alternatively or in addition, methods can include assessment of DEA distribution in GA and/or polymeric precursors of GA, and using, having, storing, and/or providing information resulting from such assessment, e.g., for the selection, review (e.g., quality control), and/or manufacture of GA and/or polymeric precursors of GA. In some embodiments, the present disclosure includes making recommendations for the selection, review (e.g., quality control), and/or manufacture of GA and/or polymeric precursors of GA based on the methods provided herein.

In some embodiments, methods disclosed herein contemplate observation or assessment of the distribution of one, two, three, or four distinct DEA-modified amino acids (e.g., DEA-modified alanine, DEA-modified lysine, DEA-modified glutamic acid, and/or DEA-modified tyrosine), peptides containing DEA-modified alanine, DEA-modified lysine, DEA-modified glutamic acid, and/or DEA-modified tyrosine, and/or total DEA-modified amino acids and/or peptides in GA and/or polymeric precursors of GA, and use of such observation or assessment to select, monitor, assess, and/or evaluate GA and/or polymeric precursors of GA. For example, in some embodiments, a level of one, two, three, four, or total DEA-modified amino acid or peptide in GA or polymeric precursors of GA can be observed, assessed, and/or compared with a level of one, two, or three other DEA-modified amino acids or peptides in the GA or polymeric precursors of GA, a level of total DEA-modified amino acid in the GA or polymeric precursors of GA, and/or a reference value or standard. In some embodiments, the distribution of one, two, three, or four distinct DEA-modified amino acids and/or peptides in GA and/or polymeric precursors of GA can be compared to total DEA in the GA and/or polymeric precursors of GA. In some embodiments, levels of one, two, three, or four distinct DEA-modified amino acids can be expressed as a percentage of total DEA-modified amino acids in GA and/or polymeric precursors of GA. In some embodiments, action may be taken if the distribution of DEA-modified amino acids in the GA and/or polymeric precursors of GA comply with or are consistent with a defined or approved standard. In some embodiments, methods include comparison of the distribution of DEA modified amino acids in the GA and/or polymeric precursors of GA with defined or values, standards or levels of DEA modified amino acids (e.g., Federal Drug Administration (FDA) approved or commissioned DA approved values, standards or levels). Data points can be expressed and/or compared as ratios, levels, relative levels, e.g., as long as the data points can be compared. In some cases, conversion of data points can be performed to facilitate comparison.

As described above, the present disclosure provides methods for accurately and/or precisely assessing (e.g., measuring, analyzing, detecting, determining, evaluating, estimating, and/or predicting) DEA distribution e.g., including the level(s) (e.g., level, relative level, concentration, amount, and/or mass) of one or more of DEA-modified alanine, DEA-modified lysine, DEA-modified glutamic acid, DEA-modified tyrosine, and/or total DEA-modified amino acids in GA and/or a polymeric precursor of GA. Methods can include comparison of such distribution to a reference standard for GA and/or a polymeric precursor of GA (e.g., a reference standard showing distribution of one or more of DEA-modified alanine, DEA-modified lysine, DEA-modified glutamic acid, and DEA-modified tyrosine in GA and/or a polymeric precursor of GA). Because DEA distribution on the C-terminus of a portion of amino acids of GA is a characteristic, hallmark, and/or signature (e.g., a structural signature) of GA and/or the GA production process, information pertaining to the distribution, of DEA can be used to select, monitor, assess, and/or evaluate a GA process and/or batch quality.

In some embodiments, the present disclosure includes assessment of level(s) (e.g., level, relative level, concentration, amount, and/or mass) of one or more of DEA-modified alanine, DEA-modified lysine, DEA-modified glutamic acid, and DEA-modified tyrosine, and/or total DEA-modified amino acids in GA and/or a polymeric precursor of GA to a reference value or standard using the 'isobaric tag for relative and absolute quantitation (iTRAQ),' e.g., using mTRAQ®. iTRAQ is based on the covalent labeling of the N-terminus and side-chain amines of peptides from protein digestions with tags of varying mass. These samples can then be pooled and optionally fractionated by nano liquid chromatography and analyzed, for example, by tandem mass spectrometry (MS/MS). The fragmentation of the attached tag generates a low molecular mass reporter ion that can be used to relatively quantify the peptides and the proteins from which they originated. For example, in some instances, methods can include labeling GA and/or polymeric precursors of GA, mixing labeled GA and/or polymeric precursors of GA with a reference sample comprising detectably distinct labeling, and analyzing the mixture. Labeled GA and/or polymeric precursors and reference sample comprising detectably distinct labeling can be assessed separately or together.

Methods discussed herein can be used to identify differences in GA materials not observed using conventional methods (e.g., by analysis of molar mass and/or amino acid composition). For example, by evaluating diethylamide distribution in GA or a polymeric precursor of GA, one can identify non-conforming compositions during or following the GA manufacturing process. Alternatively or in addition, methods can be used to confirm consistency between initiation kinetics in GA production processes (e.g., to determine equivalence or compare consistency in initiation kinetics between lots of material). For example, comparisons can be made between two or more batches or lots of GA, e.g., manufactured by different manufacturers, two or more batches or lots of GA manufactured at different locations, two or more batches or lots of GA manufactured at different times, two or more batches or lots of GA manufactured different processes, and/or two or more batches or lots of GA manufactured using altered or modified initiation kinetics. The compositions and methods herein can also be used in quality control, e.g., to compare and/or confirm batch-to-batch consistency between lots made by a consistent process.

As used herein, GA can include GA and/or polymeric precursors of GA, including, but not limited to, compositions comprising GA and/or or polymeric precursors of GA; a batch or batches, a sample or samples, a lot or lots of GA or polymeric precursors of GA, filtrates comprising GA and/or polymeric precursors of GA; and/or mother liquors (e.g., left after drying) comprising GA and/or polymeric precursors of GA and/or low molecular weight peptides related to GA. A batch of GA and/or a polymeric precursor of GA can be all or part of the product of a GA manufacturing process (e.g., all or part of a single manufacturing process or run). In some cases, one batch is analyzed. In some cases, two or more batches are analyzed. In other cases, multiple samples taken from a single batch are analyzed. A composition containing GA can be a drug substance (DS) (also known as an active pharmaceutical ingredient (API), a drug product (DP), or a process intermediate. GA can also include GA before or after formulation as a drug product.

Polymeric precursors of GA can include but are not limited to, e.g., Intermediate-1, Intermediate-2, and/or Intermediate-3 described in the manufacturing process above. For example, polymeric precursors of GA can include peptides generated during the production of GA, e.g., following the initiation step and up to the deprotection step.

The term "amino acid" is not limited to naturally occurring amino acids, but can include amino acid derivatives and/or amino acid analogs. For example, in an amino acid copolymer comprising tyrosine amino acids, one or more of the amino acids can be a homotyrosine. In addition, an amino acid modified at its C-terminus to incorporate diethylamide is referred to herein as an amino acid or a diethylamide-modified amino acid. Further, a peptide having one or more non-peptide or peptidomimetic bonds between two adjacent residues is included within the scope of this disclosure.

As noted above, GA includes four naturally occurring amino acids: L-glutamic acid, L-alanine, L-tyrosine, and L-lysine, each of which can be modified by the addition of DEA. The present disclosure includes assessing (e.g., measuring, analyzing, detecting, determining, evaluating, estimating, and/or predicting) DEA distribution, e.g., the distribution (e.g., proportions, levels, relative levels, and/or ratios) of one or more (e.g., including two or more, three or more, and four) of DEA-modified alanine, DEA-modified lysine, DEA-modified glutamic acid, and DEA-modified tyrosine in GA and/or a polymeric precursor of GA.

In some embodiments, the distribution of DEA in GA or polymeric precursors of GA (e.g., whether determined, provided, or obtained) can be compared to the values provided in Table 1. In some instances, the distribution of DEA in GA or a polymeric precursor of GA can correlate with, can be equal (e.g., about equal), and/or can be equivalent (e.g., about equivalent) to a level or ratio shown in Table 1.

Values in Table 1 relate to DEA distribution in GA and/or polymeric precursors of GA, including DEA-modified amino acids, DEA-modified peptides, and/or combinations of DEA-modified amino acids and DEA-modified peptides. These values are expressed as percent or percentages (%), which, as a skilled practitioner will appreciate, indicate a level relative to total (e.g., the actual (e.g., measured), predicted, or theoretical total) DEA-modified amino acid in the sample (including DEA-modified amino acids and/or DEA-modified peptides). All values shown in Table 1 are approximate or about and can include, e.g., +/−10, 9, 8, 7, 6, 5, 4, 3, 2, 1, 0.75, 0.5, 0.25, 0.2, 0.15, 0.1, 0.075, 0.05, 0.025, 0.01.

Table 1 includes value (%) ranges and range mean (shown in parentheses) for or relating to each of Tyr-DEA, Glu-DEA, Lys-DEA, and Ala-DEA, shown as W (superscript), Y (superscript), and Z (superscript). As used in Table 1, W refers to mean (< >) minimum and mean maximum values, derived from Table 2 (see Example 1). Y refers to the minimum W value multiplied by 0.75 and the maximum W value multiplied by 1.25. Z refers to the minimum W value multiplied by 0.9 and the maximum W value multiplied by 1.1.

Shaded rows in Table 1 show ratios calculated from W values. a (superscript) ratios are normalized against the mean of the w range for Tyr-DEA. b (superscript) ratios are normalized against the mean of the w range for Glu-DEA. c (superscript) ratios are normalized against the mean of the w range for Ala-DEA. "X" indicates data points that can be compared.

Use of Table 1 can include, but is not limited to, for example, comparison of a value or range shown in rows L with DEA distribution in GA and/or polymeric precursors of GA; and/or comparison of one or more of the values or ranges shown in rows L and one or more of the values or ranges shown in columns P with DEA distribution in GA and/or a polymeric precursor of GA. In some instances, W values in column L are compared with W values in rows P, Y values in column L are compared with Y values in rows P, and/or, Z values in column L are compared with Z values in rows P. In some instances, a value or range representing any one or more (e.g., one, two, three, four) of Tyr-DEA, Glu-DEA, Lys-DEA, and/or Ala-DEA can be compared to any one or more other feature of GA, including, for example, molecular weight, chain ends, total number of chains, and/or total DEA, etc.

For example, use of Table 1 can include comparison of data points for one, two, three, four, and/or total DEA-modified amino acids shown in Table 1 with DEA distribution in GA and/or polymeric precursors of GA. By way of non-limiting example, use of Table 1 can include comparison of a data point for one DEA-modified amino acid shown in Table 1, e.g., expressed as a percentage of total DEA, with a level of the same DEA-modified amino acid, e.g., expressed in the same or a comparable format, in GA and/or polymeric precursors of GA.

For instance, as conveyed by Table 1, comparison can include comparison of 60-76% Ala-DEA (see column L, Ala-DEA, W range) with DEA distribution in GA and/or a polymeric precursor thereof. Alternatively or in addition, comparison can include comparison of 60-76% Ala-DEA (see column L, Ala-DEA, W range) and 11-17% Lys-DEA (see rows P, Lys-DEA, W range) with DEA distribution in GA and/or a polymeric precursor thereof. In some instances, correlation, equality, and/or equivalence between such values in Table 1 and DEA distribution in the GA and/or the polymeric precursor thereof can facilitate selection of the GA and/or the polymeric precursor thereof. As indicated above, data points shown in Table 1 can be compared to levels of DEA-modified amino acids in GA and/or polymeric precursors of GA that have been determined (e.g., physically determined), predicted, estimated (e.g., based on average levels of DEA-modified amino acids in two or more lots or batches of GA and/or polymeric precursors of DEA; by using diethylamine recovered from GA manufacture to calculate or estimate total DEA incorporation into the GA and/or polymeric precursors of GA; and/or by using diethylamine recovered from GA manufacture to calculate or estimate DEA-modified amino acids in GA and/or polymeric precursors of GA), provided, and/or recorded.

Thus, as discussed in more detail below, Table 1 can be used to assess DEA distribution in GA and/or a polymeric precursor thereof by comparing the DEA distribution in the GA and/or a polymeric precursor thereof with the values in Table 1.

TABLE 1

| | | % | Ala-DEA<br>59.5-76.1 (67.8)<br>60-76 (68)$^w$<br>45-95 (70)$^y$<br>54-84 (69)$^z$ | | Lys-DEA<br>11.3-17.3 (14.3)<br>11-17 (14)$^w$<br>9-22 (15)$^y$<br>10-19 (15)$^z$ | | Glu-DEA<br>9.9-15.0 (12.5)<br>10-15 (13)$^w$<br>7-19 (13)$^y$<br>9-17 (13)$^z$ | | Tyr-DEA<br>4.8-7.2 (6.0)<br>5-7 (6)$^w$<br>4-9(6)$^y$<br>4-8(6)$^z$ | | Total |
|---|---|---|---|---|---|---|---|---|---|---|---|
| | | | | and/or | | and/or | | and/or | | and/or | 100 |
| L (Optionally compare with P) | Tyr-DEA | 4.8-7.2 (6.0)<br>5-7 (6)$^w$<br>4-9(6)$^y$<br>4-8(6)$^z$ | X | | X | | X | | — | | X |
| | | 1$^a$ | 10 | | 2 | | 2 | | — | | |
| | Glu-DEA | 9.9-15.0 (12.5)<br>10-15 (13)$^w$<br>7-19 (13)$^y$<br>9-17 (13)$^z$ | X | | X | | — | | X | | X |
| | | 1$^b$ | 4 | | 0.9 | | — | | 0.5 | | |
| | Lys-DEA | 11.3-17.3 (14.3)<br>11-17 (14)$^w$<br>9-22 (15)$^y$<br>10-19 (15)$^z$ | X | | — | | X | | X | | X |
| | | 1$^c$ | 5 | | — | | 1 | | 0.5 | | |
| | Ala-DEA | 59.5-76.1 (67.8)<br>60-76 (68)$^w$<br>45-95 (70)$^y$<br>54-84 (69)$^z$ | — | | X | | X | | X | | X |
| | | 1$^d$ | — | | 0.2 | | 0.2 | | 0.1 | | |

In some instances, the values shown in Table 1 are reference values (e.g., a specification for commercial release of GA) and methods can include comparing the distribution of DEA in GA and/or a polymeric precursor to the reference values in Table 1. For example, the methods herein generally include obtaining or providing GA and/or a polymeric precursor and/or obtaining data regarding DEA distribution in GA and/or a polymeric precursor of GA, assessing the distribution of DEA therein, and comparing the distribution of DEA to Table 1. Distribution of one or more, including all, of Ala-DEA, Lys-DEA, Glu-DEA, Tyr-DEA, and/or total DEA can be assessed. Total DEA is the sum of DEA-modified amino acids in GA and/or polymeric precursors of GA. Total DEA can be actual (e.g., based on one or more measurements of DEA in the GA and/or polymeric precursor) or theoretical (e.g., based on an average value for total DEA in GA and/or a specific stage in the GA manufacturing process (e.g., total DEA in Intermediate-1, Intermediate-2, and/or Intermediate-3)). DEA-modified amino acids can be measured separately and/or together and the sum of DEA-modified amino acids can be determined therefrom. Prior to measuring total DEA, DEA can be removed from amino acids and/or peptides, e.g., by hydrolysis. For example, DEA can be measured after hydrolysis of GA and/or polymeric precursors of GA. For polymeric precursors of GA, total DEA can include the sum of DEA-modified amino acids at a defined stage in the GA manufacturing process.

DEA distribution can be assessed by review of DEA levels in GA or polymeric precursors. Levels can include the level of one or more of Ala-DEA, Lys-DEA, Glu-DEA, Tyr-DEA, and/or total DEA as independent values (e.g., mass or volume) or as relative values (e.g., the level of one or more DEA modified amino acid relative to the level of one or more of the other DEA modified amino acids or total DEA (e.g., percentage or concentration)). Levels can include: the level of Ala-DEA or the level of Ala-DEA and the level of one or more of Lys-DEA, Glu-DEA, Tyr-DEA, and/or total DEA; the level of Lys-DEA or the level of Lys-DEA and the level of one or more of Ala-DEA, Glu-DEA, Tyr-DEA, and/or total DEA; the level of Glu-DEA, or the level of Glu-DEA and the level of one or more of Lys-DEA, Ala-DEA, Tyr-DEA, and/or total DEA; and/or the level of Tyr-DEA, or the level of Tyr-DEA and the level of one or more of Lys-DEA, Ala-DEA, Ala-DEA, and/or total DEA.

Levels of DEA in the GA and/or a polymeric precursor can be expressed in any suitable units. For example, levels can be expressed as percent values (as exemplified in Table 1) and/or as ratios of two or more, three or more, four or more, or all of Ala-DEA, Lys-DEA, Glu-DEA, Tyr-DEA, and/or total DEA. In addition, units can be converted to facilitate comparison with Table 1 using techniques known in the art and/or reasonable skill. Values can also be represented by any other useful parameter by converting the distribution, proportions, relative levels, and/or ratios of diethylamide into such parameters. For example, the values can be converted to relative molar amounts and/or mole % or percent of chains. Unit conversion is not required if equivalence can be determined.

GA and/or a polymeric precursor of GA can be selected if the distribution of DEA in the GA or the polymeric precursor of GA correlates with, is equal (e.g., about equal) to, and/or is equivalent (e.g., about equivalent) to, a level or ratio shown in Table 1. For example, methods can include comparing the distribution of DEA in GA and/or a polymeric precursor of GA with Table 1, and selecting the GA and/or the polymeric precursor if the distribution of DEA in the GA or the polymeric precursor of GA correlates with, is equal (e.g., about equal) to, and/or is equivalent (e.g., about equivalent) to, a level or ratio shown in Table 1.

As shown in Table 1, the distribution, of one or more DEA-modified amino acids in GA and/or its polymeric precursors can be, for example:

a distribution of DEA-modified alanine:DEA-modified lysine:DEA-modified glutamic acid:DEA-modified tyrosine of or of about 62-68%:12-15%:14-16%:6-7%, e.g., wherein the sum of the distribution is 100%;

a distribution of DEA-modified alanine:DEA-modified lysine:DEA-modified glutamic acid:DEA-modified tyrosine of or of about 47-85%:9-19%:11-20%:5-9%, e.g., wherein the sum of the distribution is 100%;

a distribution of DEA-modified alanine:DEA-modified lysine:DEA-modified glutamic acid:DEA-modified tyrosine of or of about 56-75%:11-17%:13-18%:5-8%, e.g., wherein the sum of the distribution is 100%;

a ratio of two or more of DEA-modified alanine:DEA-modified lysine:DEA-modified glutamic acid:DEA-modified tyrosine, wherein the value for DEA-modified alanine is about 10, the value for DEA-modified lysine is about 2, the value for DEA-modified glutamic acid is about 2, and the value of DEA-modified tyrosine is about 1, wherein about can be ±0.1, ±0.2, ±0.3, ±0.4, and ±0.5; a ratio of about DEA-modified alanine:DEA-modified lysine:DEA-modified glutamic acid:DEA-modified tyrosine of or of about (e.g., wherein about can be ±0.1, ±0.2, ±0.3, ±0.4, and ±0.5) 10:2:2:1;

a ratio of two or more of DEA-modified alanine:DEA-modified lysine:DEA-modified glutamic acid:DEA-modified tyrosine, wherein the value for DEA-modified alanine is about 4, the value for DEA-modified lysine is about 0.9, the value for DEA-modified glutamic acid is about 1, and the value of DEA-modified tyrosine is about 0.5, wherein about can be ±0.1, ±0.2, ±0.3, ±0.4, and ±0.5;

a ratio of about DEA-modified alanine:DEA-modified lysine:DEA-modified glutamic acid:DEA-modified tyrosine of or of about (e.g., wherein about can be ±0.1, ±0.2, ±0.3, ±0.4, and ±0.5) 4:0.9:1:0.5;

a ratio of two or more of DEA-modified alanine:DEA-modified lysine:DEA-modified glutamic acid:DEA-modified tyrosine, wherein the value for DEA-modified alanine is about 5, the value for DEA-modified lysine is about 1, the value for DEA-modified glutamic acid is about 1, and the value of DEA-modified tyrosine is about 0.5, wherein about can be ±0.1, ±0.2, ±0.3, ±0.4, and ±0.5;

a ratio of about DEA-modified alanine:DEA-modified lysine:DEA-modified glutamic acid:DEA-modified tyrosine of or of about (e.g., wherein about can be ±0.1, ±0.2, ±0.3, ±0.4, and ±0.5) 5:1:1:0.5;

a ratio of two or more of DEA-modified alanine:DEA-modified lysine:DEA-modified glutamic acid:DEA-modified tyrosine, wherein the value for DEA-modified alanine is about 1, the value for DEA-modified lysine is about 0.2, the value for DEA-modified glutamic acid is about 0.2, and the value of DEA-modified tyrosine is about 0.1, wherein about can be ±0.1, ±0.2, ±0.3, ±0.4, and ±0.5; and/or a ratio of about DEA-modified alanine:DEA-modified lysine:DEA-modified glutamic acid:DEA-modified tyrosine of or of about (e.g., wherein about can be ±0.1, ±0.2, ±0.3, ±0.4, and ±0.5) 1:0.2:0.2:0.1.

In some embodiments, methods do not include assessment of diethylamine and/or distribution of DEA-modified amino acids in GA and/or a polymeric precursor of GA does not include diethylamine. Unless methods include cleaving DEA from the C-terminal of DEA-modified amino acids, methods do not include assessing DEA not associated with amino acid (free DEA).

Selection of GA and/or polymeric precursors of GA can include selecting (e.g., for use or further processing) a sample of GA or a polymeric precursor of GA based on distribution of DEA-modified amino acids in the sample (e.g., based on comparison of distribution of DEA-modified amino acids in the sample with at least one (e.g., one, two, three, four, or more) reference value(s) shown in Table 1). For example, the methods can be used to: select a sample of GA or a polymeric precursor thereof for further use; select (e.g., as suitable for sale or for administration (e.g., injection) to a human) a sample of GA or a polymeric precursor thereof; classify, accept, release, process into drug product a sample of GA or a polymeric precursor thereof; select a sample of GA or a polymeric precursor thereof for shipment, moving to a new location, formulating, labeling, packaging, selling, offering for sale, releasing into commerce; and/or select a sample of GA or a polymeric precursor thereof for use in a manufacturing process for GA. Methods can also include assessment of Intermediate-1 and use of the Intermediate-1 in a manufacturing process for GA precursor if the level of one or more of Ala-DEA, Lys-DEA, Glu-DEA, and/or Tyr-DEA in the Intermediate-1 is equal (e.g., about equal) to, equivalent (e.g., about equivalent) to, and/or consistent with a reference value, wherein the reference value is a reference value disclosed in Table 1; assessment of Intermediate-2 and use of the Intermediate-2 in a manufacturing process for GA precursor if the level of one or more of Ala-DEA, Lys-DEA, Glu-DEA, and/or Tyr-DEA in the Intermediate-2 is equal (e.g., about equal) to, equivalent (e.g., about equivalent) to, and/or consistent with a reference value, wherein the reference value is a reference value disclosed in Table 1; and/or assessment of Intermediate-3 and use of the Intermediate-3 in a manufacturing process for GA precursor if the level of one or more of Ala-DEA, Lys-DEA, Glu-DEA, and/or Tyr-DEA in the Intermediate-3 is equal (e.g., about equal) to, equivalent (e.g., about equivalent) to, and/or consistent with a reference value, wherein the reference value is a reference value disclosed in Table 1.

In some embodiments, a sample of GA or a polymeric precursor of GA can be selected if the distribution of DEA in the GA has a preselected relationship with, is equal (e.g., about equal) to, is equivalent (e.g., about equivalent) to, and/or is consistent with the levels or ratios shown in Table 1. In some embodiments, methods can include selecting GA or a polymeric precursor if the level of one or more of Ala-DEA, Lys-DEA, Glu-DEA, and/or Tyr-DEA is equal (e.g., about equal) to, equivalent (e.g., about equivalent) to, and/or consistent with a reference value, wherein the reference value is a reference value disclosed in Table 1.

The methods described herein can also include selecting to discard, withhold, reprocess through a previous manufacturing step, or discontinue use of, GA or a polymeric precursor of GA, for example, if the distribution of DEA in the GA or the polymeric precursor do not meet a preselected relationship, are not equal to, are not equivalent with, and/or are not consistent with the levels shown in Table 1.

Methods for Determining DEA Distribution

In some embodiments, the present disclosure includes measuring, assessing, determining or detecting one or more of DEA-modified alanine, DEA-modified lysine, DEA-modified glutamic acid, DEA-modified tyrosine, and/or total DEA-modified amino acid in a sample of GA and/or a polymeric precursor of GA. Accordingly, the disclosure provides methods for accurately and/or precisely measuring, assessing, determining or detecting one or more of DEA-modified alanine, DEA-modified lysine, DEA-modified glutamic acid, DEA-modified tyrosine, and/or total DEA-modified amino acid in a sample of GA and/or a polymeric precursor of GA. Other methods not explicitly disclosed herein may also be used so long as they allow at least detection (e.g., specific detection) of one or more of DEA-modified alanine, DEA-modified lysine, DEA-modified glutamic acid, DEA-modified tyrosine, and/or total DEA-modified amino acid in a sample of GA and/or a polymeric precursor of GA.

Referring to FIG. 1, a flow diagram is provided illustrating one non-limiting exemplary embodiment of a method for assessing DEA distribution. In STEP O, a sample comprising GA or a polymeric precursor thereof is provided or obtained. In STEP 1, the cleaving step, the GA or a polymeric precursor thereof in the sample is cleaved to produce in the sample shorter or smaller fragments (e.g., smaller peptide fragments) of the GA or the polymeric precursor without removing (e.g., without substantially removing or with consistently minimal removal of) C-terminal DEA from the GA or the polymeric precursor. Fragments can include, e.g., 1, 2, 3, 4, 5, 6, 7, 8, 9, 10, or more amino acid residues. In STEP 2, the labeling step, detectable standards (e.g., DEA-modified detectable peptides that represent some or all of the fragments produced in STEP 1) are added (e.g., in known amounts) to the sample containing shorter or smaller fragments of GA or the precursor to produce a labeled sample. In STEP 3, the separation step, fragments and labeled standards in the labeled sample are separated into subpopulations with shared or common properties. In STEP 4, the detection step, the subpopulations are assessed using method capable of detecting and distinguishing the detectable standards and the fragments of GA and the polymeric precursor. The detectable standards can then be subtracted and the distribution of diethylamide-modified amino acids determined.

In some embodiments, methods can include one or more (e.g., one, two, three, all, or substantially all) of STEP O, STEP 1, STEP 2, STEP 3, and STEP 4, e.g., performed in any order that results in determination of DEA distribution, including variations and/or modifications of STEPS 1, 2, 3, and/or 4.

STEP O

In some embodiments, methods include providing or obtaining a sample(s) comprising GA or a polymeric precursor thereof can include GA and/or polymeric precursors of GA, e.g., as described above, including, but not limited to, compositions comprising GA and/or or polymeric precursors of GA; a batch or batches, a sample or samples, and/or a lot or lots of GA or a polymeric precursors of GA, filtrates comprising GA and/or polymeric precursors of GA; and/or mother liquors (e.g., left after drying) comprising GA and/or polymeric precursors of GA. Samples may be chemically modified to convert diethylamides into new chemical groups. Such methods can include, but are not limited to, modification of diethylamides into chemically distinct groups resistant to cleavage (e.g., reduction of diethylamides to alcohols).

STEP 1

In some embodiments, methods include STEP 1, the cleaving step. In some embodiments, STEP 1 can be performed using any treatment or method, or combination thereof that can cleave (e.g., specifically cleave) peptide bonds without removing diethylamide (e.g., without substantially removing diethylamide). Such treatments or methods can yield single amino acid residues and/or cleaved peptides, e.g., peptides containing fewer amino acid residues than would be present in the same peptide absent the treatment of method. Such cleaved peptides can include 2, 3, 4, 5, 6, 7, 8, 9, 10, or more amino acid residues.

Each of the species resulting from the cleaving step (e.g., the species of single amino acid residues and/or the species of cleaved peptides), which can be collectively referred to as fragments, can include sub-species, e.g., DEA-modified fragments, that include DEA-modified alanine:DEA-modified lysine:DEA-modified glutamic acid:DEA-modified tyrosine and cleaved peptides that include DEA-modified alanine: DEA-modified lysine:DEA-modified glutamic acid:DEA-modified tyrosine. For example, cleaved peptides can include 2, 3, 4, 5, 6, 7, 8, 9, 10, or more amino acid residues, wherein the C-terminal amino acid residue is DEA-modified alanine: DEA-modified lysine:DEA-modified glutamic acid:DEA-modified tyrosine. Suitable methods and treatments can include, e.g., one or more of enzymatically, chemically, and/or physically cleaving the GA. In some embodiments, the average number of amino acids these DEA-modified fragments is 4 or less amino acids, 3 or less amino acids, or two or less amino acids.

Exemplary enzymatic methods for use in STEP 1 can include contacting the GA or the polymeric precursor with an enzyme that can cleave or digest peptide bonds in the GA or the polymeric precursor without removing or substantially removing DEA therefrom. Suitable enzymes can include one or more proteases, and suitable proteases can include, but are not limited to, for example, one or more of trypsin, chymotrypsin, elastase, ficin, papain, pepsin, plasmin, thermolysin, endopeptidase, proteinase K, ox bile, lemon pectin, horseradish peroxidase, glu-c, endo lys-C, carboxypeptidase, calpain, and subtilisin. In some embodiments, the enzyme is removed following cleavage of the GA, e.g., by filtration.

Exemplary chemical methods for use in STEP 1 can include contacting or treating the GA or the polymeric precursor with a chemical or compound that can cleave peptide bonds in the GA or the polymeric precursor without removing or substantially removing DEA therefrom. Suitable chemicals can include, but are not limited to, e.g., one or more of a strong acid, an alkali base, and phenylisothiocyanate.

Exemplary physical methods for use in STEP 1 can include treating the GA or the polymeric precursor using conditions that cleave or digest peptide bonds in the GA or the polymeric precursor without removing or substantially removing DEA therefrom. Suitable conditions or treatments can include, but are not limited to, e.g., one or more of boiling, sonicating, and shearing.

In some embodiments, STEP 1 can include producing a sample that contains only DEA-modified amino acids and/or DEA-modified peptides. For example, the methods can include isolating or purifying DEA-modified amino acids and/or DEA-modified peptides; removing amino acids and/or peptides that do not include a DEA-modified amino acid; and/or removing diethylamine.

STEP 2

In some embodiments, methods can include STEP 2, a labeling step. In some embodiments, STEP 2 can include supplementing or adding detectable standards to the sample. The detectable standards can include molecules that are representative of each of the DEA-modified amino acid residues and/or DEA-modified cleaved peptides produced or expected to be produced by the cleaving step. In some instances, such molecules can include DEA-modified amino acids or DEA-modified peptides that are identical (e.g., chemically identical) to the fragments obtained in the cleaving step, but that can be distinguished from those fragments (e.g., due to one or more distinct or unique properties (e.g., the presence of one or more detectable markers)) and/or that can be detected. In some instances, the detectable standards can be chemically distinct (e.g., can include chemically distinct DEA, chemically distinct carboxylates, and/or chemically distinct peptide bonds).

In some embodiments, the detectable standards can have substantially the same retention time under chromatography (e.g., liquid chromatography) as the fragments produced in the cleavage step, but with distinct or distinguishable peaks on a chromatograph. For example, the detectable standards can be isotopically labeled DEA-modified amino acids and/or DEA-modified peptides that represent one or more of the DEA-modified amino acid residues and/or DEA-modified cleaved peptides produced or expected to be produced by the cleaving step. In some instances, isotopically labeled DEA-modified amino acids and/or DEA-modified peptides that represent each of the DEA-modified amino acid residues and/or DEA-modified cleaved peptides produced or expected to be produced by the cleaving step. In some cases, isotopically labeled DEA-modified amino acids or peptides can include, e.g., 1, 2, 3, or more amino acids, wherein one of the amino acids (e.g., the C-terminal amino acid) is a DEA-modified amino acid. In some cases, the concentration or amount of labeled standard added or in the sample is known, e.g., to facilitate later accounting for or subtraction of the labeled standards.

Alternatively or in addition, STEP 2 can include manipulation of DEA-modified amino acids to produce DEA-modified amino acids that can be distinguished from other DEA-modified amino acids and/or that can be distinguished from amino acids and/or peptides that do not include DEA. For example, DEA-modified alanine can be modified to be distinguishable from one or more of DEA-modified lysine, DEA-modified glutamic acid, and/or DEA-modified tyrosine; DEA-modified lysine can be modified to be distinguishable from one or more of DEA-modified alanine, DEA-modified glutamic acid, and/or DEA-modified tyrosine; DEA-modified glutamic acid can be modified to be distinguishable from one or more of DEA-modified alanine, DEA-modified lysine, and/or DEA-modified tyrosine; DEA-modified tyrosine can be modified to be distinguishable from one or more of DEA-modified alanine, DEA-modified glutamic acid, and/or DEA-modified lysine; and/or one or more of DEA-modified alanine, DEA-modified lysine, DEA-modified glutamic acid, and/or DEA-modified tyrosine can be modified to be distinguishable from amino acids and/or peptides that do not include DEA. Such methods can include, but are not limited to, for example, modifying DEA to chemically distinct groups, changing carboxylates to chemically distinct groups, and/or changing peptide bonds to chemically distinct groups.

STEP 3

In some embodiments, methods can include STEP 3, a separation step. In some embodiments, STEP 3 can include any method whereby fragments of GA are separated into subpopulations of macromolecules. For example, the separation can be based on one or more of a chemical, physical, and/or functional property shared by a class of macromolecules within the fragments of GA, e.g., size, charge, hydrophobicity, or any other shared property. In some instances, the fragments can be separated into subpopulations of amino acids and peptides that include diethylamide-modified C-termini and those that do not. The subpopulation of fragments that include diethylamide-modified C-termini can also be separated (e.g., further separated) into DEA-modified alanine:DEA-modified lysine:DEA-modified glutamic acid: DEA-modified tyrosine. Suitable methods can include, but are not limited to, e.g., analysis of migration through a gel, size, molecular weight, migration through an applied electrical field, charge, hydrophobicity, boiling point, and solubility, as well as chromatographically separating by size and/or charge, and obtaining the fragments of GA and the labeled standards. Suitable methods for performing this step can include, but are not limited to, for example, gas chromatography (GC), GC-MS, liquid chromatography, liquid chromatography mass spectroscopy, ion chromatography, mass spectroscopy, nuclear magnetic resonance (NMR), antibody methods, Raman spectroscopy, capillary electrophoresis, multidimensional NMR spectroscopy, extraction, and/or precipitation. Single or multiple separation steps can be used.

STEP 4

In some embodiments, methods can include STEP 4, a detection step. In some embodiments, STEP 4 can include any method that can detect the fragments of GA and the labeled standards and that can distinguish the fragments of GA from the labeled standards. Suitable methods can include, but are not limited to, for example, mass spectroscopy analysis, MRM detection, tandem mass spectrophotometry (MS/MS), NMR analysis, infrared spectroscopy, gel electrophoresis, emission spectroscopy, UV-vis spectroscopy, Raman spectroscopy, fluorescence spectroscopy, emission spectroscopy, and/or antibody detection. In some instances, the detection step includes MS-MRM detection, e.g., which selects targeted parent ions for fragmentation and then searches for specific fragment (daughter) ions. Only species that match the parent and/or daughter ions of the targeted species are detected, giving rise to high specificity with low background.

The detection step can provide levels of DEA-modified alanine:DEA-modified lysine:DEA-modified glutamic acid:DEA-modified tyrosine in the fragments of GA and in the GA. Such levels can include levels of the labeled standard. However, as the labeled standard can be distinguished from unlabeled DEA-modified amino acids and because the concentration or amount of labeled standard added is known, labeled standard can be subtracted. In embodiments where isotopically labeled DEA-modified amino acids or peptides are used as the labeled standards, the standards can be designed to elute at the same time and/or ionize with the same efficiency as the DEA modified amino acids in the fragments of GA. However, because of the isotopic enrichment, the standards have distinct MRM signatures from the target species. Thus, in such embodiments, the relative difference in area between the MRM signals of the standards to the MRM signals of the target species are directly proportional to the differences in concentrations. Therefore, since the concentrations of the standards are known, the concentrations of the target species can be directly determined from the ratios of the MRM signals.

Detected levels of DEA-modified alanine:DEA-modified lysine:DEA-modified glutamic acid:DEA-modified tyrosine can include various species. Such species can include, for example, DEA-modified amino acids and DEA-modified peptides. DEA modified peptides can include 2 or more amino acids (e.g., 2, 3, 4, 5, 6, 7, 8, 9, 10, or more amino acids). DEA-modified peptides can be referred to collectively by reference to their DEA-modified amino acid, as is done throughout the present disclosure. For example, any peptides with a C-terminal DEA modified alanine can be referred to as a diethylamide-modified alanine peptide or Ala-DEA. Alternatively or in addition, the sum of each of the distinct levels of each of the diethylamide modified peptides can be determined to calculate total DEA-modified alanine:DEA-modified lysine:DEA-modified glutamic acid:DEA-modified tyrosine in the GA or polymeric precursor.

Alternatively or in addition, methods can include direct detection of DEA, e.g., with or without use of the cleaving and/or labeling steps discussed above. Such methods include detection of DEA associated with amino acid (e.g., DEA-modified amino acids and/or peptides (bound DEA)) and DEA not associated with amino acid (free DEA). Such methods can include a first optional separation to obtain a population of DEA-modified peptides from GA or a polymeric precursor of GA, and a second separation to obtain distinct populations of peptides containing C-terminal Ala-DEA, Lys-DEA, Glu-DEA or Tyr-DEA. In some instances, any free DEA can be removed before detection. DEA can then be separately detected in one or more, including all, of the distinct populations, e.g., without the need to further determine the species of DEA-modified peptide (e.g., DEA detected in the Ala-DEA population is DEA associated with Ala). Detection can include direct assessment of bound DEA using techniques known in the art and disclosed herein. Detection can also include removal (e.g., cleavage) of bound DEA from DEA-modified peptides using techniques known in the art and disclosed herein to obtain free DEA. Free DEA can then be detected using methods known in the art. Detected DEA from one or more of the populations can then be compared to a reference value. GA or polymeric precursors can be selected if the distribution of DEA is equal (e.g., about equal) to, equivalent (e.g., about equivalent) to, and/or consistent with a reference value, wherein the reference value is a reference value disclosed in Table 1.

In some embodiments, DEA detected using the methods disclosed herein can be compared to diethylamine. Methods for detection of diethylamine are known in the art (see, e.g., US 2007/0054857). The steps recited herein do not indicate or imply order. Accordingly, the steps can be performed contemporaneously or in any order that allows a result to be obtained. For example, the cleaving step can be performed before, after, or about simultaneously (e.g., simultaneously) with the labeling step. Similarly, the separating step can be performed before or about simultaneously (e.g., simultaneously) with the detecting step. These values can be represented as distributions, proportions, relative levels, and/or ratios of DEA in GA or polymeric precursor (see above).

EXAMPLES

The invention is further described in the following examples, which do not limit the scope of the invention described in the claims.

Example 1

Comparison of Reference Listed Drug

As shown herein, the distribution of diethylamide (DEA) in the C-termini of glatiramer acetate (GA) and the sequence context of DEA in GA, namely the identity of the adjacent amino acid residue, is a direct consequence of the initiation kinetics applied in the manufacturing of GA. The differential reactivity of the NCAs (initiation rate constants) and proportions of NCAs control the proportions of amino acid diethylamides produced. The initiation step is the only step in the manufacturing process that creates diethylamides. Subsequent processing can remove some of the diethylamides.

Multiple lots of COPAXONE™ were analyzed for DEA-modified alanine:DEA-modified lysine:DEA-modified glutamic acid:DEA-modified tyrosine using the method illustrated in FIG. 1. The mean, minimum, and maximum values obtained from this analysis are shown in Table 2.

TABLE 2

Comparison of Multiple Lots of Glatiramer Acetate RLD

| | % Ala-DEA | % Lys-DEA | % Glu-DEA | % Tyr-DEA |
|---|---|---|---|---|
| Mean | 67.8 | 14.3 | 12.5 | 6.0 |
| Minimum | 59.5 | 11.3 | 9.9 | 4.8 |
| Maximum | 76.1 | 17.3 | 15.0 | 7.2 |

This data suggests that the distribution of DEA within GA can serve as a signature of GA. The consistency of these data also suggests that the methods disclosed herein are accurate.

It should be noted that the ratio of DEA modified amino acids differs from the ratio of amino acids in GA as shown in Table 3. For example, while Lys represents 33.8% of the amino acids in GA, Lys-DEA represents only 11.3-17.3% of the DEA modified amino acids in GA. In contrast, Ala represents 42.7% of the amino acids in GA, but Ala-DEA represents 59.5-76.1% of the DEA modified amino acids in GA.

TABLE 3

Comparison of amino acid ratios and DEA-modified amino acids

| Amino acid | % in GA | % DEA modified in GA (mean) |
|---|---|---|
| Glu | 14.1 | 9.9-15.0 (12.5) |
| Ala | 42.7 | 59.5-76.1 (67.8) |
| Tyr | 9.5 | 4.8-7.2 (6.0) |
| Lys | 33.8 | 11.3-17.3 (14.3) |

Methods disclosed herein were also shown to be precise and sensitive. For example, the process was shown to be robust in that changes in digestion and analytical conditions could be accommodated without adversely impacting sensitivity, precision, and/or accuracy. Use of different lots of columns and/or enzyme also did not adversely impact sensitivity, precision, and/or accuracy. This suggests that the methods disclosed herein are precise. Furthermore, changing the initial NCA charge proportions produced significant changes in the diethylamide proportions in the expected directions (e.g. decreasing the initial charge of Ala NCA decreased the proportion of Ala-DEA in the product). This suggests the methods are capable of detecting changes in initiation kinetics used in the manufacture of GA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising;
(a) providing a batch of glatiramer acetate;
(b) obtaining one or more samples of the batch of glatiramer acetate; and
(c) measuring, in at least one of the one or more samples of the batch, the level of diethylamide-modified fragments selected from the group consisting of: fragments having a diethylamide-modified alanine, fragments having a diethylamide-modified lysine, fragments having a diethylamide-modified glutamic acid, and fragments having a diethylamide-modified tyrosine using a method that comprises:
(i) cleaving the glatiramer acetate to generate fragments;
(ii) combining the fragments with detectably labeled diethylamide-modified peptide standards;
(iii) fractioning the mixture of fragments and detectably labeled diethylamide-modified peptide standards to generate subpopulations; and
(iv) detecting the fragments and detectably labeled diethylamide-modified peptide standards in one or more subpopulations by a method selected from mass spectroscopy analysis, MS-MRM detection, tandem mass spectrophotometry (MS/MS), and NMR.

2. The method of claim 1 wherein the fragments comprise peptides and amino acids.

3. The method of claim 1 wherein the average length of the fragments is less than 4 amino acids.

4. The method of claim 1 wherein the detectably labeled diethylamide-modified peptide standards comprise diethylamide-modified peptides and diethylamide-modified amino acids.

5. The method of claim 1 wherein the step of providing a batch of glatiramer acetate comprises: (i) polymerizing N-carboxy anhydrides of L-alanine, benzyl-protected L-glutamic acid, trifluoroacetic acid (TFA)-protected L-lysine, and L-tyrosine to generate a protected copolymer (Intermediate-1); (ii) treating the Intermediate-1 to generate Intermediate-2 by partially depolymerizing the protected copolymer and deprotecting benzyl protected L-glutamic acid; (iii) treating the Intermediate-2 to generate Intermediate-3 by deprotecting TFA-protected L-lysines; and (iv) treating the Intermediate-3 to generate glatiramer acetate.

6. The method of claim 5 wherein step (a) comprises contacting the polymerizing N-carboxy anhydrides of L-alanine, benzyl-protected L-glutamic acid, trifluoroacetic acid (TFA)-protected L-lysine, and L-tyrosine with diethylamine.

7. The method of claim 5 wherein step (ii) comprises contacting the Intermediate-1 with phenol treated 33% HBr/acetic acid.

8. The method of claim 5 wherein step (iii) comprises contacting the Intermediate-2 piperdine.

9. The method of claim 5 wherein step (iv) comprises diafiltration and ultrafiltration.

10. The method of claim 1 wherein the batch of glatiramer acetate is a batch of glatiramer acetate drug substance.

11. The method of claim 1 comprising measuring the level of two or more of: fragments having a diethylamide-modified alanine, fragments having a diethylamide-modified lysine, and fragments having a diethylamide-modified glutamic acid and fragments having a diethylamide-modified tyrosine.

12. The method of claim 11 comprising measuring the level of three or more of: fragments having a diethylamide-modified alanine, fragments having a diethylamide-modified lysine, and fragments having a diethylamide-modified glutamic acid and fragments having a diethylamide-modified tyrosine.

13. The method of claim 11 comprising measuring the level of: fragments having a diethylamide-modified alanine, fragments having a diethylamide-modified lysine, and fragments having a diethylamide-modified glutamic acid and fragments having a diethylamide-modified tyrosine.

* * * * *

UNITED STATES PATENT AND TRADEMARK OFFICE
CERTIFICATE OF CORRECTION

PATENT NO. : 8,765,911 B2
APPLICATION NO. : 13/692490
DATED : July 1, 2014
INVENTOR(S) : Cuihua Liu et al.

Page 1 of 1

It is certified that error appears in the above-identified patent and that said Letters Patent is hereby corrected as shown below:

1.) Title Page 2, item (56) References Cited.– OTHER PUBLICATIONS, Column 2, Line 47: delete "Anitmicribial" and insert -- Antimicrobial --.

In the Claims

2.) Column 27, Line 55: delete "comprising;" and insert -- comprising: --.

3.) Column 28, Line 42: delete "piperdine" and insert -- piperidine --.

Signed and Sealed this
Twenty-first Day of October, 2014

Michelle K. Lee
*Deputy Director of the United States Patent and Trademark Office*